(12) United States Patent
Wang et al.

(10) Patent No.: US 9,567,612 B2
(45) Date of Patent: Feb. 14, 2017

(54) CORN DEGERMING ETHANOL FERMENTATION PROCESSES

(75) Inventors: Hui Wang, Des Moines, IA (US); Tong Wang, Ames, IA (US); Lawrence A. Johnson, Ames, IA (US)

(73) Assignee: Hui Wang, Urbandale, IA (US)

( * ) Notice: Subject to any disclaimer, the term of this patent is extended or adjusted under 35 U.S.C. 154(b) by 358 days.

(21) Appl. No.: 12/798,193

(22) Filed: Mar. 31, 2010

(65) Prior Publication Data

US 2010/0260918 A1 Oct. 14, 2010

Related U.S. Application Data

(60) Provisional application No. 61/165,681, filed on Apr. 1, 2009.

(51) Int. Cl.

| | | |
|---|---|---|
| C12P 7/06 | (2006.01) | |
| A23D 9/02 | (2006.01) | |
| C11B 1/02 | (2006.01) | |
| C12F 3/10 | (2006.01) | |
| A23L 1/172 | (2006.01) | |
| A23L 1/105 | (2006.01) | |

(52) U.S. Cl.
CPC . *C12P 7/06* (2013.01); *A23D 9/02* (2013.01); *A23K 10/38* (2016.05); *A23L 7/104* (2016.08); *A23L 7/115* (2016.08); *A23L 7/152* (2016.08); *C11B 1/025* (2013.01); *C12F 3/10* (2013.01); *A23L 1/105* (2013.01); *A23L 1/172* (2013.01); *Y02E 50/17* (2013.01); *Y02P 60/873* (2015.11)

(58) Field of Classification Search
CPC ............ A23L 1/172; A23L 1/105; A23K 1/06
See application file for complete search history.

(56) References Cited

U.S. PATENT DOCUMENTS

| | | | |
|---|---|---|---|
| 1,456,540 A * | 5/1923 | Ditman | 536/57 |
| 2,135,462 A * | 11/1938 | Boroughs | 426/11 |
| 2,698,825 A * | 1/1955 | Frankel | 435/95 |
| 3,474,722 A * | 10/1969 | Stewart et al. | 426/442 |
| 4,106,487 A | 8/1978 | Randall | |
| 4,330,625 A * | 5/1982 | Miller et al. | 435/161 |
| 5,231,017 A * | 7/1993 | Lantero et al. | 435/161 |
| 6,254,914 B1 | 7/2001 | Singh | |
| 6,403,084 B1 * | 6/2002 | Chan et al. | 424/93.45 |
| 6,899,910 B2 | 5/2005 | Johnston | |
| 6,927,048 B2 * | 8/2005 | Verser et al. | 435/161 |
| 7,452,425 B1 * | 11/2008 | Langhauser | 127/40 |
| 2002/0022252 A1 * | 2/2002 | Johnston et al. | 435/72 |
| 2002/0151733 A1 * | 10/2002 | Ulrich et al. | 554/9 |
| 2003/0232109 A1 * | 12/2003 | Dawley et al. | 426/53 |
| 2004/0023349 A1 * | 2/2004 | Bisgaard-Frantzen et al. | 435/161 |
| 2004/0234649 A1 * | 11/2004 | Lewis et al. | 426/31 |
| 2007/0014905 A1 * | 1/2007 | Chen et al. | 426/490 |
| 2007/0178567 A1 * | 8/2007 | Lewis | 435/161 |

OTHER PUBLICATIONS

Dooley et al. "Distillers Grain Handbook: A Guide . . . " A Report for the Indiana Corn Marketing Council Dec. 2008 http://incorn.org/index2.php?option=com_content&do_pdf=1&id=43 pp. 1-5.*

* cited by examiner

*Primary Examiner* — Felicia King

(57) ABSTRACT

The invention presents novel corn fermentation processes that remove the oil-rich fraction either during or after fermentation instead of before fermentation as usual. Besides recovery of high value oil-rich fraction of the corn, the processes also produce other value-added co-products such as that with high fiber or high protein but low oil contents.

4 Claims, 15 Drawing Sheets

CORN DEGERMING ETHANOL FERMENTATION PROCESSES

CROSS REFERENCE TO RELATED APPLICATION

This non-provisional application claims the benefit of U.S. Provisional Application No. 61/165,681, filed Apr. 1, 2009.

BACKGROUND OF THE INVENTION

This invention involves methods to recover germ fractions during or after ethanol fermentation using starch-containing corn or corn components as feedstock. By recovering germ during or after fermentation, new value-added products including germ fractions, fiber fraction and protein-enriched fraction are produced:

The corn kernel contains about 70 percent starch, 9 percent protein, 10 percent fiber, and 4 percent oil, with the rest mineral or other minor components, in three distinctive parts: (1) the pericarp; (2) the endosperm; and (3) the germ, which account for about 6 percent, 83 percent, and 11 percent of the total mass of the kernel, respectively. The pericarp is a strong fibrous seed skin, consisting primarily of coarse fiber. The endosperm consists of mainly powderous starch and gluten protein, which serve as energy reserve for seed germination and seedling growth. The germ is the embryo of the corn kernel. It consists primarily of oil and germ protein.

Corn is an important grain in US and the world as a raw material for food, feed and industrial applications. In the past decade or so, corn becomes the primary feedstock for fuel ethanol production in US. According to the Renewable Fuels Association (RFA), 22.5 percent of the total US corn crop (equivalent to about 3.0 billion bushels) in 2007/08 was used to make fuel ethanol. Of the 3.0 billion bushels of corn, about 82 percent or 2.5 billion bushels were processed by the dry-grind ethanol process, with the rest by wet milling ethanol process. Though its development seems reach a plateau in recent years (around year 2009), corn-based fuel ethanol production, especially the dry-grind fuel ethanol fermentation, is a well-established industry.

The major difference between the dry-grind ethanol process and the wet milling ethanol process is that dry-grind breaks the corn kernel into flour or meals and then ferment the whole mixture without fractionation of individual components while the wet-milling process separate the major constitutes of the corn into germ, fiber, gluten protein first and only the starch fraction is needed in fermentation to produce ethanol.

In many of the prior art dry-grind processes, the corn kernels are ground into flour using a hammer mill. The starch in the flour mixture is hydrolyzed into fermentable sugars by enzymes, and subsequently converted into ethanol by yeast. The fermented mash is then distilled to recover the ethanol. After the removal of ethanol, the mash, called whole stillage is separate into two fractions by centrifugation or decanting. One is wet cake, which is a mixture of non-fermentable solids of the corn (the oil, fiber, and protein), the other is thin stillage, which consists of water, soluble, dispersable fine solids and oil. The thin stillage is concentrated into thick stillage, a syrup-like mixture, by evaporation, and then combined with the wet cake, and dried together to produce distillers dried grains with solubles, or DDGS. Majority of the DDGS is used as low-valued cattle feed due to its high fiber content. The market for DDGS is saturated.

The dry-grind ethanol processes of the prior art which do not contain a degerming step are unable to capture the germ. The complexing of the starch with oil in dry-grind ethanol processes also reduces starch fermentability.

The wet-milling ethanol processes in prior art are the further fermentation after the conventional wet milling in which corn is fractionated into four basic components: starch, protein, fiber, and germ by using a series of grinding, separation and purification steps in an aqueous system. Only the starch fraction is used in fermentation to make ethanol. Besides starch or starch-derives (including ethanol), wet milling produces gluten meal, fiber, and germs. Germ can be further processed into edible oil, which is the most valuable component from the corn. However, wet milling requires sophisticated equipment, high capital investment, and high inputs of energy and water. Usually food grade starch and its derivatives are the main products from wet milling products due to their relatively higher values. Fuel ethanol is only a side product from a typical wet-milling company. Wet mills are usually operated at large scale with total investment near or over one billion US Dollars in order to achieve commercial efficiency. The wet-milling is a stable business dominated by about 13 companies in the world.

Compared to wet-milling ethanol process, the dry-grind ethanol process is much simpler, requiring less expensive equipment, and less capital input, thus majority of the increased capacity of fuel ethanol production is from dry-grind process, and over 75 percent of the fuel ethanol is produced in this way. The dry-grind ethanol co-product, DDGS, however, is less valuable than co-products of wet milling. Increasing the profitability of the dry-grind ethanol industry without major modifications of its infrastructure remains a challenge.

One possible strategy is to recover the oil from the downstream liquid phase of the conventional dry-grind ethanol process. However, once the oil-rich germ is broken into small pieces, the oil mixes with and is diluted by the oil-lean components including fiber, endosperm proteins, and residual starch, making it difficult to be recovered. Another problem is that the oil from the conventional dry-grind process is highly degraded, usually contains high level of free fatty acid (in a range of 9 to 15 percent).

Recovering the oil in the form of intact germ as that from wet-milling within the dry-grind industry establishment is probably the only way to ensure high yield and good oil quality.

Many of the prior-art degerming processes have been proposed over the past decade. These processes can be divided into two categories, one is dry-degerming processes and the other wet-degerming processes.

In many of the prior art dry-degerming processes, the corn kernels are moistened with water to increase their moisture content. The slightly softened corn kernels are broken into the pericarp, germ, and endosperm pieces using a coarse mill. The pieces are then screened and aspirated to separate the germ from lighter pericarp and the heavier endosperm pieces. The oil content in the germ fraction from dry degerming processes is only about 20 percent compared to about 40 percent from wet milling, and less than half of the total germ is recovered. This is because the separation of germ and other components is not complete. Germ fractions from dry-degerming contain significant amounts of endosperm and other components; at the same time more than one half of the germ is lost to the endosperm fraction.

The losses of starch in the germ fraction and germ in the endosperm fraction reduce both ethanol yield and oil recovery, which compromises the economy of these processes.

Many of the prior art wet-degerming processes are modifications of conventional wet-milling process. They usually involve soaking or steeping the corn in water for a prolonged time period followed by size-reduction and fractionation in liquid phase. Water helps soften the corn and acts as a suspension medium where the kernel can be broken open to release the germ without major damage. Since oil-rich germ has lower density than the slurry medium, the germ can be isolated by floatation, such as hydrocloning or centrifugation method. After germ is removed, the starch-containing germ-free fraction is usually fermented together with at least another component (fiber or gluten protein) without further concentration or purification of the starch. The steeping or soaking time can be reduced from 24-36 hours at 52° C. in conventional wet milling to less than 12 hours at 59° C. in wet-degerming processes. The oil content in the germ is about 30 percentage. This technique is known as "Quick Germ Process". When the pericarp (coarse fiber) is also recovered before fermentation, the process is termed "Quick Germ Quick Fiber". There are other minor modifications to these processes, such as in "Enzymatic Milling" or "E-Milling", where the enzyme was used to replace part or all chemicals including sulfur dioxide.

Nevertheless, these prior art wet-degerming techniques have yet to achieve widespread adoption by the dry-grind corn ethanol industry. One reason is that they still need major wet-milling equipment, including steeping tanks, degermer mills and hydroclones, which are expensive for small dry-grind plants.

These prior art processes (either dry degerming or wet degerming) all involve germ separation before the fermentation started, i.e. at the front-end. They all have lower ethanol yield than the conventional dry-grind process because some starch is unavoidably lost in the germ or fiber fractions. The oil content in the germ from is lower than that from the conventional wet milling process.

Therefore there is a need to develop new degerming processes for the dry-grind ethanol industry to achieve better fractionation (higher purity components), higher processing efficiency, easier adaptability, and to help meet the increasing demand for both food and fuel from corn.

In our invented new degerming processes the germ fraction is recovered during or after ethanol fermentation. The new processes in this invention have a few significant advantages compared to prior art front-end wet-degerming processes: 1) the total ethanol yield is higher; 2) the total germ yield is higher and the recovery of the germ is easier since the fermentation "eats away" the starch between germ and coarse fiber/endosperm proteins; 3) the coarse fiber exists in larger pieces, which can be recovered more easily; and 4) since the germ is recovered during or after fermentation, it can be processed differently and it needs less expensive equipments, such as screening apparatus, aspirators, etc.

Our invention in which the germ fraction is recovered during or after fermentation is not a simple switch of different processing steps during corn refining, because the intact germ has to go through prolonged fermentation treatment, which has different physical, mechanical, biological and chemical environments compared to that in prior art. Our invention is possible only because we studied and discovered that by proper treatments, the germ can remain physical intact during the fermentation process with little or no chemical degradation to the germ oil. Part of the data is incorporated in Example 2 of the EXAMPLES section.

SUMMARY OF THE INVENTION

According to the present invention, there are provided methods related to novel corn degerming fermentation processes. In one aspect of the invention, corn kernels comprising protein, fiber, an oil-rich component and starch is provided. A corn mixture is produced, where the corn mixture includes water and protein, fiber, germ and starch. The corn is fermented to produce ethanol and the fermented slurry is separated. A stillage fraction and a wet cake fraction are obtained from the separated and fermented corn slurry. The wet cake fraction is separated and germ fraction and a cake meal fraction are obtained.

Further according to the present invention, there are provided additional methods related to novel fermentation processes. A corn material including protein, fiber, germ and, starch is provided. A corn mixture with water is produced. The corn mixture is fermented and separated approximately simultaneously and a germ fraction is obtained from the separated fermented mixture.

BRIEF DESCRIPTION OF THE DRAWINGS

FIG. 1 (*b*) shows the prior art processes that the germ is recovered before fermentation.

FIG. 1 (*c*) shows our invention that the germ is recovered after or during fermentation.

DETAILED DESCRIPTION OF THE INVENTION

Figure 1:
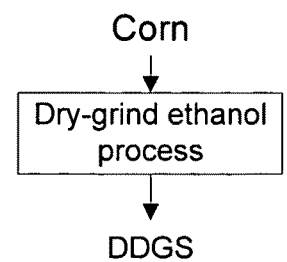
FIG. 1 (*a*) shows the prior art dry-grind ethanol processes without the germ recovery.
Figure 1:
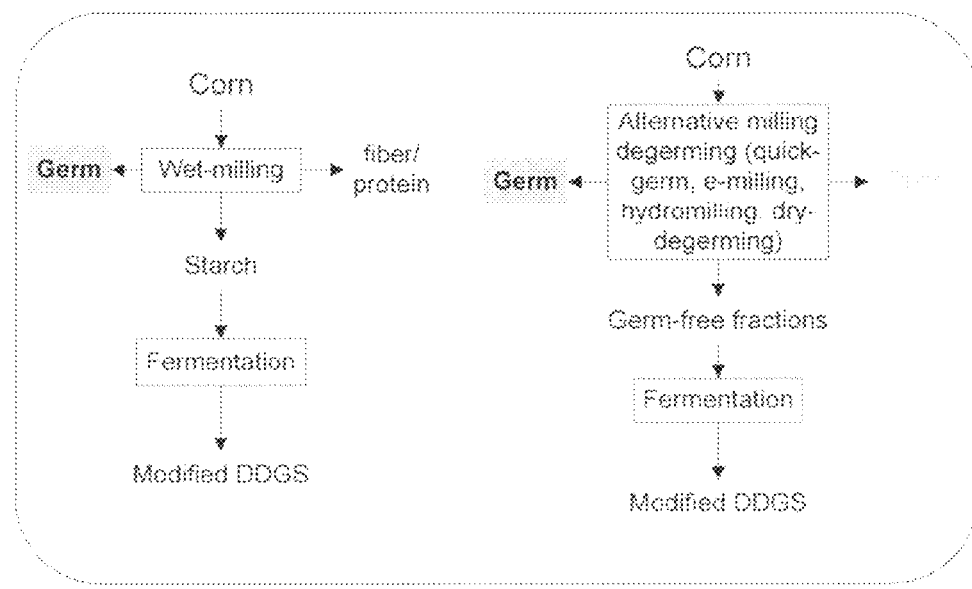
Figure 1:
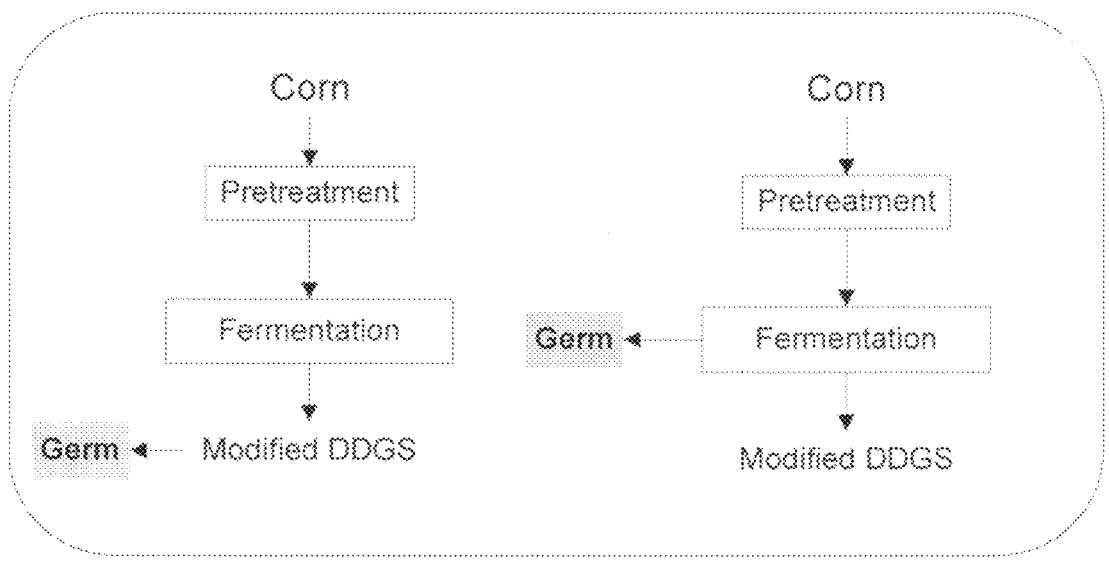

The following description is merely exemplary in nature and is not intended to limit the present disclosure, application, or uses.

In the novel processes of the present invention, the germs may be removed during or after fermentation. In various aspects of the present invention, the germs may be removed concurrently with the ethanol fermentation process, after the fermentation is finished, after distillation of the whole beer, during decanting, or from the modified dried distillers grains with solubles (modified DDGS). Due to the removal of the germs concurrently or after fermentation, streams of new co-products will be produced by the processes of the present invention.

The corn used in the fermentation process of the present invention can be natural, chemically modified, or genetically modified.

The economic viability of producing ethanol in a corn dry-grind process is therefore significantly improved with the process of the present invention. Germ, the source of valuable edible oil or feedstock for producing biodiesel and corn germ meal, is produced.

Commercial wet-milling processes use only starch fraction to produce fuel ethanol. Other known processes remove the oil-rich fraction before the fermentation starts. The processes of the present invention remove the oil-rich fractions after the inoculation of yeasts. The present invention processes remove the germs either during different stages of fermentation, or after fermentation.

The processes for removing the germs of the present invention are easier for industry to adopt and adapt, more efficient than and produce better co-products than known processes for removing the germs.

Compared to commercial wet-milling process, the processes of the present invention do not need huge investment or extensive energy and water usage. Compared to commercial dry-milling process, the processes of the present invention reduce further the energy and capital investment. In aspects of the present invention, the spent stream may be combined with fuel ethanol fermentation, which not only eliminates potential negative impacts on the environment but also saves water and utilizes the starch typically found in the germ fraction of alternative processes.

In some aspects of the present invention, the novel degerming processes help alleviate the corn biofuel vs. food dilemma by extracting food ingredients from the corn refining process while at the same time potentially saving more energy and water.

In one aspect of the present invention, referred to as tail-end degerming, the germ remains intact during the whole dry-grind fermentation process. During the tail-end degerming processes of the present invention, all of the starch is effectively converted into ethanol. The intact germ is recovered at the tail-end, from the dried grains.

The tail-end degerming processes of the present invention remove germ after fermentation and ethanol removal. The germ may be removed from the whole stillage, the wet cake, or the dried grain stages. The tail-end degerming processes of the present invention also produce good germ separation, clean fractionation of fiber, capture of protein enriched co-products, and have similar or higher ethanol yield compared to conventional processes.

The tail-end degerming processes of the present invention have multiple advantages compared to the conventional dry-grind and wet-mill processes. The tail-end degerming processes of the present invention produce a high yield of oil from the germ fractions, cleaner germ compared to conventional processes, valuable co-products with enriched protein, fiber, oil in different fractions which can be easily tailored to produce feedstuffs with higher feed efficiency for different livestock which has different nutrition needs, and at the same time have a similar or higher ethanol yield and fermentation time as conventional dry-grind process. Microbial contamination is not an issue in the degerming ethanol processes of the present invention, as compared to non-cooking or low heat treatment conventional processes. The tail-end degerming processes of the present invention utilize the conventional dry-grind plant infrastructure without major modification, are easily adapted by industry and have less energy costs.

As used herein "process stream" or "stream" means any process stream(s) generated in the ethanol processes of the present invention.

Figure 2:
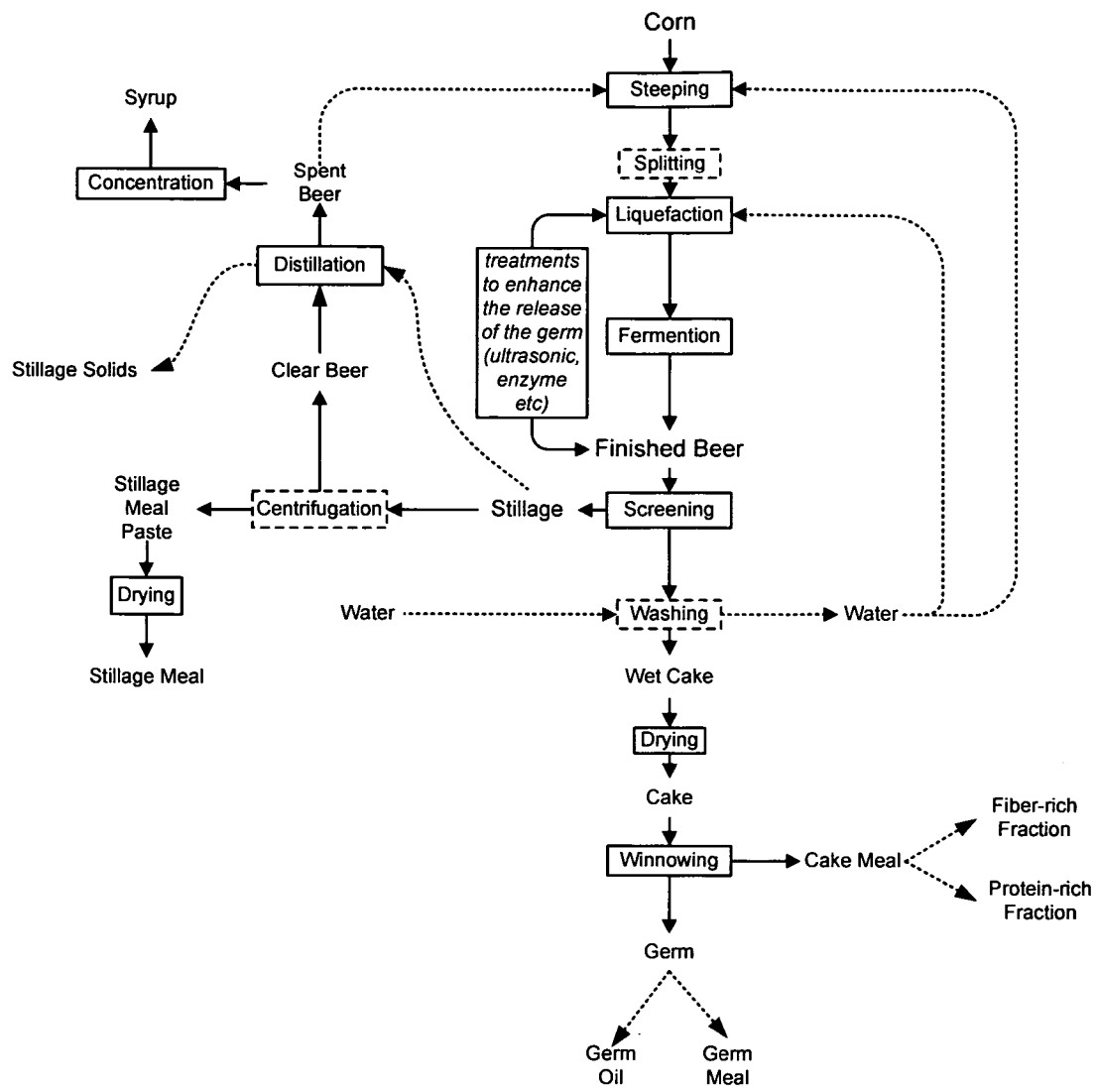
FIG. 2 shows an embodiment of the tail-end degerming dry-grind ethanol process.
Figure 6:
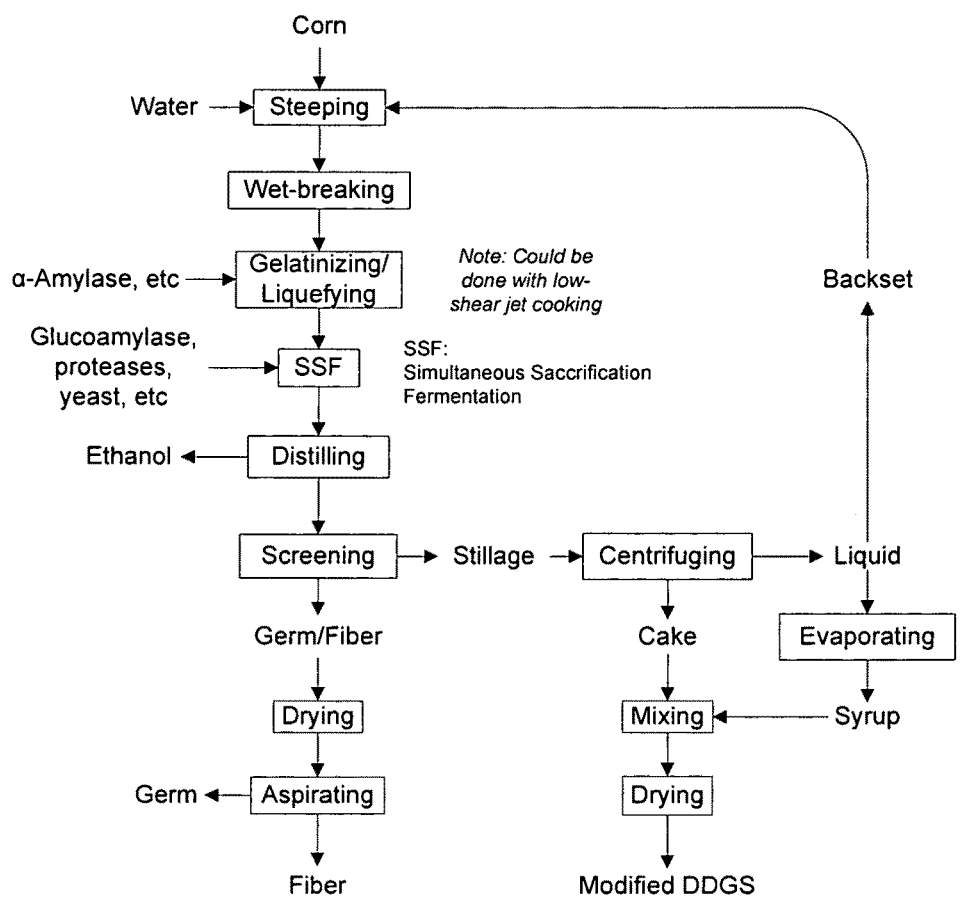
FIG. 6 shows an embodiment of tail-end degerming ethanol process with separate steeping, breaking, gelatinizing-liquefying steps and a simultaneous saccharification and fermentation step.
Figure 7:
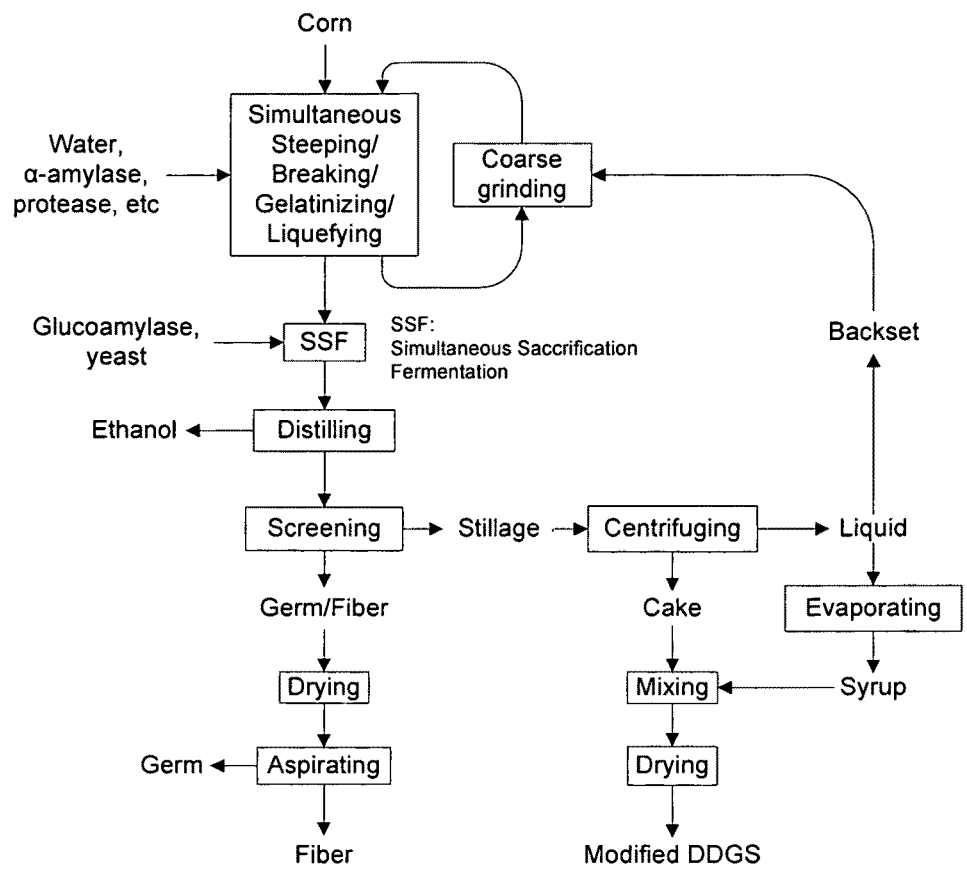
FIG. 7 shows an embodiment of the tail-end degerming ethanol process with simultaneous steeping, breaking, and gelatinizing-liquefying steps and a simultaneous saccharification and fermentation step.
Figure 8:
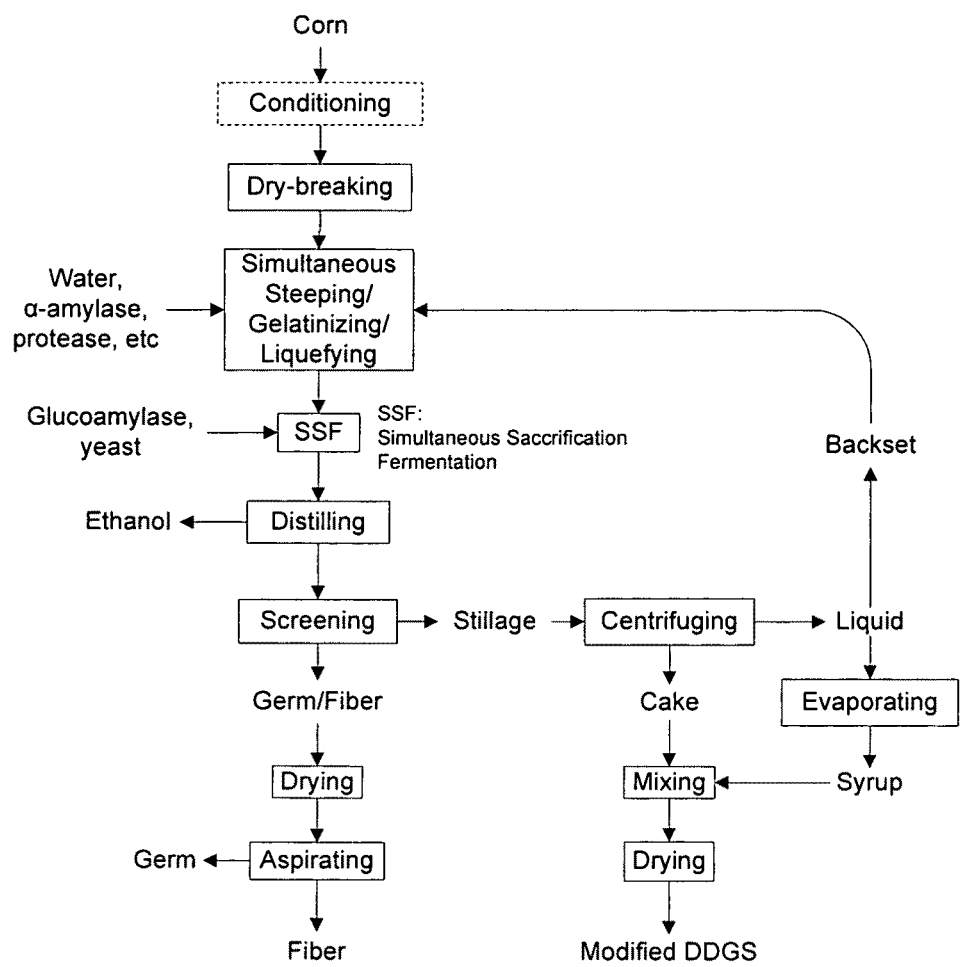
FIG. 8 shows an embodiment of the tail-end degerming ethanol process with simultaneous steeping and gelatinizing-liquefying steps and a simultaneous saccharification and fermentation step.

Referring now to FIGS. 2 and 6-8, multiple embodiments of the tail-end degerming ethanol process of the present invention are shown. FIG. 2 shows one aspect of the invention, referred to as the tail-end degerming dry-grind ethanol process. FIG. 6 shows one aspect of the invention, referred to as the tail-end degerming with separate steeping, breaking, gelatinizing-liquefying SSF (simultaneous saccharification fermentation). FIG. 7 shows one aspect of the invention, referred to as the tail-end degerming with, simultaneous steeping, breaking, gelatinizing-liquefying SSF. FIG. 8 shows one aspect of the invention, referred to as the tail-end degerming with dry-breaking simultaneous steeping-gelatinizing-liquefying SSF. Referring now to FIGS. 2 and 6-8, multiple embodiments and aspects of the tail-end degerming process of the present invention are shown and described.

In one aspect of the present invention, the corn is initially put through a steeping (soaking) process. In one aspect of the present invention, the corn kernels are steeped using steam-like cooking. In another aspect of the present invention, the corn kernels are steeped in water. In one aspect of the invention, the corn kernels are steeped or soaked in a short period of time, for example 1-3 hours, in order to hydrate the germ. When the corn kernel is opened after a short soak period, damage to the germ is reduced. Germ recovery ease is also improved.

Steeping the corn kernels causes physical changes in the various components of the corn kernel that facilitates subsequent process steps. In one aspect of the invention, the corn kernels may be steeped in recycled water from downstream processes. The corn kernels may be steeped in a steeping reactor to produce an aqueous slurry of steeped corn kernels.

Any steeping reactor suitable for use and known to one of skill in the art may be used in accordance with the present invention. In one aspect of the invention, the steeping may occur in a steeping reactor similar to the device described in U.S. Pat. No. 7,452,425 or U.S. Pat. No. 4,106,487. The reactor is a vertical cylinder with a cone at its bottom. The kernels are added at the top and evenly distributed across the surface area. The kernels then move downward through the water in plug flow by the force of gravity. Any lightweight materials added with the whole corn kernels (cobs, stalks, etc.) are trapped with the whole corn kernels and move along with them down the reactor. A center collector at the top of the steeping reactor collects water for recycle and steep water solids blow down. The center collector is continuously cleaned by the moving corn. The moving corn acts as a filter medium and traps materials that might choke the corn screen. The steep water collected at the screen on the top of the reactor may be heated to kill any objectionable bacteria flushed from the reactor or added from downstream processing and also to maintain the temperature of the reactor. The water may be added on the side of the reactor just above the top of the cone to expand the plug flow mass of corn to facilitate removal of the corn as a slurry at the bottom of the cone. Fresh water is distributed in the cone to maintain the counter-current washing of the corn.

In one aspect of the invention, the water used in the steeping step may be recycled from downstream processes. For example, the water may be recycled as a byproduct from the stillage centrifuging step; the cake washing step; and the distillation step.

In one aspect of the present invention, the corn kernels, after going through the steeping or soaking process, are opened up using physical, chemical, and or enzymatic treatments without extensive damage to the germ.

The steeped corn kernels may undergo a cracking, splitting or wet-breaking process to open up the corn kernel. Corn kernels may be broken, cracked or split using a variety of means known to one of skill in the art. For example, a Bauer disc mill, a flaking mill, or a Waring blender may be used to open the corn kernel. Optimally, any method used to open up the corn kernel effectively opens the corn kernel without breaking the germ.

The present invention may utilize a variety of treatments to enhance the release of the germ from the corn kernel. For example, process steps to enhance the release of germ from the kernel may include ultrasonic treatments and or enzyme treatments.

In one aspect of the invention, the opened corn kernel may go through a gelatinizing process step. The starch may be gelatinized by heating the opened corn to a temperature of about 66 to 95° C. or above. An effective amount of amylase enzymes may also be added when applicable. In one aspect of this invention, α-amylase may be used as an amylase enzyme in this process step. This step is known as gelatinization because the heat gelatinizes some or all the starch. This step may also be known as cooking or as preliminary liquefaction because the gelatinized starch becomes liquefied (water soluble).

The corn slurry may also go through a liquefying step, which may be performed after the splitting or wet-breaking step or after the liquefying step. The liquefaction step gelatinizes all the starch granules, breaks the starch down into smaller fragments, and makes the starch more accessible for downstream processing. The liquefaction step also helps to loosen any residual starch from the other components and reduces the size of the protein particles. In another aspect of the invention, the liquefying step and the gelatinizing step are performed simultaneously. The liquefying step may be performed simultaneously with the gelatinizing step or separately.

In one aspect of the invention, at this point in the process the corn slurry consists of a slurry of corn kernels, starch, protein, fiber and germ. Water may be added to the corn slurry for the liquefying step. In particular, recycled water may be used as a byproduct from the stillage centrifuging step and the cake washing step. Enzymes may be used to degrade the starch molecules during the liquefying step. Effective amounts of amylase may be added during liquefaction. The amylase enzymes reduce the length of the starch fragments generated during liquefaction. Protease enzymes may also be added during the liquefying step. The protease enzymes break down the protein matrix which, in turn, helps to free the starch.

Any liquefaction reactor suitable for use and known to one of skill in the art may be used in accordance with the present invention. In one aspect of the invention, the liquefying step may be performed in a rotary homogenizer similar to the one described in U.S. Pat. No. 7,452,425. The rotary homogenizer is a rotor-stator machine having concentric tool rings that are radial slotted and/or drilled to provide intermeshing radial surfaces. The slurry is pumped under pressure into a chamber and is then forced laterally. The slurry passes through the gaps as the rotor spins past the gaps in the stator. Flow is most pronounced when the gaps in the rotor align with the gaps in the stator. The result is a pulsing flow with a rapid succession of compressive and decompressive forces. The rotary homogenizer thus subjects the slurry to shear and cavitation forces. More particularly, the slurry may be subjected to multi-stage hydrodynamic high shear, high-frequency oscillating forces, intensive microvolume mixing, and pressure increases. The repeated compression and decompression create microcavities that are believed to burst the granules from the inside. Accordingly, treatment in a rotary homogenizer produces unique changes in the starch granule. Treatment in a rotary homogenizer produces smaller, more irregularly shaped particles containing gelatinized starch. The starch in these particles may be more completely liquefied. The starch in these particles may be easier to saccharify.

The liquefying step is carried out by preparing a slurry with the cracked corn and water. Amylase enzymes are added to initiate the liquefaction. The slurry is heated to a temperature suitable for the amylase enzyme being used. The liquefaction process of the invention is performed at conditions, e.g. pH, temperature and time, suitable for the enzyme in question. A lower liquefaction temperature means less heating is required prior to liquefaction and less cooling is needed after liquefaction. In one aspect of the invention, the liquefaction in step is performed at 60-95° C. for around 5 hours and at a pH of about 4.5 to 6.5. The pH of the slurry may by adjusted or not, depending on the properties of the enzyme(s) used. The adjusting of pH is advantageously done at the time when the amylase enzyme is added.

The liquefaction step gelatinizes all the starch granules, breaks the starch down into smaller fragments, and makes the starch more accessible for downstream processing. The liquefaction step also helps to loosen any residual starch from the other components and reduces the size of the protein particles.

Referring now to FIG. 6, in one aspect of the invention the opened, cracked or broken corn may go through a simultaneous gelatinizing and liquefying step. In another aspect of the invention, the gelatinizing and liquefying step is done with jet cooking. By way of example only, the corn may be generally heated to 125-150° C. for about 10 seconds through a jet cooker at a pressure of about 5.1 bar and then held at around 95° C. at ambient pressure for about 10 minutes. Water is generally added to the corn prior to the jet cooking. An α-amylase enzyme may also be added to the corn to liquefy the starch to oligosaccharides. The liquefied starch may then be cooled and saccharified to glucose by utilizing a glucoamylase enzyme. The glucose may be fermented primarily by yeast to ethanol with carbon dioxide as a co-product.

Referring now to FIG. 7, in one aspect of the invention the corn kernels may go through a simultaneous steeping, breaking, gelatinizing and liquefying step. During the simultaneous steeping/breaking/gelatinizing/liquefying step, water, amylase enzymes, including, but not limited to, α-amylase, and protease enzymes may be added to facilitate the steeping/breaking/gelatinizing and liquefying steps. As depicted in FIG. 7, the corn may also go through a coarse grinding step concurrently with the simultaneous steeping/breaking/gelatinizing/liquefying. The coarse grinding process step may break the corn kernels apart into fragments of pericarp (coarse fiber), soft starch, and hard starch in a matrix with protein and fine fiber, and germ. In one aspect of the invention, backset from the downstream stillage centrifuging step is added to the corn kernels during the coarse grinding step. Any coarse grinding mill suitable for use and known to one of skill in the art may be used in accordance with the present invention.

Referring now to FIG. 8, in another aspect of the invention the corn kernels may be conditioned or cleaned and then put through a dry-breaking process to open the corn kernel. In this aspect of the invention, the corn kernels are opened prior to being steeped. As depicted in FIG. 8, the cracked kernels may then go through a simultaneous steeping, gelatinizing and liquefying phase. Water, amylase enzymes, including but not limited to α-amylase, and protease enzymes may be added during the simultaneous steeping, gelatinizing and liquefying step. Backset from the downstream stillage centrifuging step may be added to the slurry during the simultaneous steeping/gelatinizing/liquefying step.

In one aspect of the invention, the corn slurry goes through a saccharification step, which cools and saccharifies the starch fragments in the corn slurry. Saccharification is the process by which the linkages between the individual saccharide units in the fragments are broken by treatment with an effective amount of a glucosidic linkage cleaving agent. Glucosidic linkage cleaving agents may include amylase enzymes such as α-amylase and glucoamylase. Other agents include pullanase and maltase.

Protease enzymes may also be added during the saccharification step. The protease enzymes break down the peptide linkages in the protein and help to convert the protein to a form that is available for the yeast and no longer prevents access of the starch-degrading enzymes to the starch. The converted protein provides the nitrogen necessary for the yeast during fermentation. The protease enzymes may also be added during fermentation, if fermentation is performed as a separate step. The saccharification process step is generally conducted at a temperature of about 57 to 63° C.

In one aspect of the invention, the corn slurry may also go through a fermentation process step. The corn slurry may be fermented in a fermentation vessel with yeast at ambient pressure form a fermentation broth. Protease enzymes may be added at this step of the process. In one aspect of the invention, the corn slurry is fermented for around 48-72 hours at a temperature of about 32 to 35° C. and a pH of about 3.8 to 5.0. In one aspect of this invention, preferably called the tail-end degerming fermentation process, the pericarp, protein, tip cap, and germ are not separated during the processing and fermentation of the starch.

After fermentation, the slurry may be referred to as finished beer. The fermentation beer is then distilled. For example, the fermentation beer may be distilled at temperatures between 80 and 100° C. and around 1.1 bar from the fermentation beer to a final ethanol concentration product. The ethanol may be further dehydrated.

Fermentation as used herein refers to the oxidation of organic compounds, such as carbohydrates, for energy derivation. Under anaerobic conditions, yeast cells produce carbon dioxide and ethanol. One molecule of glucose is converted by yeast during the fermentation process into exactly two molecules of ethanol and two molecules of carbon dioxide. This type of fermentation is commonly referred to as ethanol fermentation. Fermentation converts the glucose molecules into ethanol and carbon dioxide by the action of yeast. Fermentation is a process by which microorganisms such as yeast digest sugars from starch to produce ethanol and carbon dioxide. The basic reaction is $C_6H_{12}O_6 \rightarrow 2C_2H_5OH + 2CO_2$. Yeast reproduce aerobically (oxygen is required) but can conduct fermentation anaerobically (without oxygen). Distillation recovers the ethanol from the fermented mixture, or the finished beer. Distillation is a process in which a liquid mixture is heated to vaporize the components having the highest vapor pressures (lowest boiling points). The vapors are then condensed to produce a liquid that is enriched in the more volatile compounds (e.g. ethanol).

Fermentation products as used herein mean any substance resulting from a fermentation reaction according to the present invention. Fermentation products may comprise alcohol and a gaseous product, preferably carbon dioxide produced by the fermentation of the total fermentables. Fermentation residuals may include dissolved and/or suspended constituents from a fermentation mash. The suspended constituents may include undissolved soluble constituents, such as where the solution is supersaturated with one or more components, and/or insoluble materials present in the fermentation beer.

Referring now to FIGS. 6-8, the corn slurry may go through a simultaneous saccharification and fermentation step, referred to as SSF. When the SSF process step of the present invention is employed, there is no holding stage for the saccharification, meaning that yeast and saccharification enzymes are added essentially together. In one aspect of the invention, glucoamylase, protease and yeast are added to the SSF process step. The term "simultaneous saccharification and fermentation" or "SSF" is intended to include the contemporaneous degradation or depolymerization of a complex sugar and bioconversion of that sugar residue into ethanol by fermentation. Reduction in enzyme cost and more complete conversion of the starch can be obtained by overlapping the saccharification activity with the fermentation process. After the SSF process step, the slurry may be distilled to produce an ethanol fraction, as well as remaining water and solids.

A variety of enzymes may be used in the gelatinizing, liquefying, saccharification and fermentation steps.

Referring now to FIGS. 6-8, in one aspect of the present invention, the remaining water and solids from the fermentation or SSF slurry may then go through a separation stage, where it may be separated into stillage and germ/fiber fractions. In the tail-end degerming fermentation process of this invention, the stillage and germ/fiber fractions contain non-starch components of the corn kernel that pass through the process, such as the germ, protein, gluten, bran and fiber. The stillage and germ/fiber fractions may be separated using any technique known to one of skill in the art, including screening.

Referring now to FIG. 2, the germ/fiber fraction may also be referred to as a wet cake. After separation, the wet cake or germ/fiber fraction may be washed. In one aspect of this invention, the water used in this washing stage may be recycled for use in liquefaction and steeping stages.

Referring now to FIGS. 2 and 6-8, the stillage fraction from the separation process may then be centrifuged, which removes a portion of the solids from the stillage. The centrifuging process separates the stillage into two fractions, the first being a liquid stream and the second being the stillage meal paste or cake solids. The liquid stream typically contains a certain percentage of solids by weight, with a certain percentage being suspended solids and a certain percentage being dissolved solids. The liquid stream contains a number of valuable co-products, some of which are soluble and some of which are suspended.

Referring now to FIG. 2, in one aspect of the invention, the liquid stream may be known as clear beer. The liquid stream, or clear beer, may be converted to syrup by distilling the liquid into a spent beer fraction and a stillage solids fraction. The liquid, or the spent beer, may then be concentrated and evaporated into syrup.

Referring now to FIGS. 6-8, in one aspect of the invention, a fraction of the liquid stream, which may be referred to as backset, may be recycled and used as make-up water in the steeping stage. The backset may be a high percentage of the liquid stream, for example as much as 50 percent of the liquid stream. The balance of the liquid stream may be sent to an evaporation process where at least some of the water is removed and the dissolved and suspended solids are concentrated to syrup. The syrup may then be mixed with the stillage meal paste or cake solids and then dried to produce an animal feed referred to as modified dry distillers grains with solubles (modified DDGS).

Compared to the distillers' co-products produced by prior art ethanol processes, the processes of the present invention produce modified DDGS that is superior in nutritional content for a variety of livestock foodstuffs. The modified DDGS, or stillage meal, has enriched protein and lower fiber and residual oil contents and may easily be manufactured to produce feedstuffs with a higher feed efficiency for different livestock needs. The modified DDGS co-product of the present invention represents an improvement of the DDGS produced in the prior art ethanol processes because of its high protein content, low fiber content and low residual oil content. The modified DDGS or stillage meal may additionally have reduced heat damage.

Referring now to FIGS. 2 and 6-8, the germ/fiber fraction, or wet cake, produced from the separation stage, is sent to a drying operation to remove at least a portion of the remaining water. Referring now to FIG. 2, the cake may go through a separating step. The separating step separates the germ from the cake meal. Any separating process known to one of skill in the art may be used, including winnowing or aspirating. The germ produces germ oil and germ meal. Referring now to FIGS. 6-8, the germ/fiber fraction may be dried and then be put through an aspirating step, which separates the germ from the fiber, or cake meal.

In the tail-end degerming ethanol production process of the present invention, the separated germ remains intact during the whole dry-grind fermentation process, unlike prior art ethanol and degerming processes. The intact germ is recovered at the tail-end of the process from the dried cake and produces germ oil and germ meal. The present invention produces cleaner germ compared to the prior art degerming and ethanol processes. Due to the cleaner germ produced by the processes of the present invention, the recovery of germ oil is high and the quality of the recovered germ oil is improved compared to conventional dry-grind ethanol process. The germ oil yield is exceptionally high compared to the prior degerming and ethanol processes and is the maximal or best recovery of oil from all known fermentation processes.

In the tail-end degerming ethanol production process of the present invention, the fiber is recovered at the tail-end of the process from the germ/fiber fraction, or cake. Regarding FIGS. 6-8, the germ/fiber fraction may go through a drying and separation phase which separates the fiber from the germ, producing enriched co-products. Regarding FIG. 2, the cake may go through a separation phase to separate the germ from the cake meal. Any separating process known to one of skill in the art may be used, including winnowing or aspirating. The cake meal comprises a fiber-rich fraction and a protein-rich fraction. These fiber and protein co-products have enriched fiber and protein contents compared to fiber and protein which may be recovered from prior art processes. These enriched protein and fiber co-products can be easily tailored to produce feedstuffs with higher feed efficiency for different livestock needs.

In one aspect of the present invention, the germ may be recovered during corn ethanol fermentation. The processes of the present invention, in which the recovery of germ during fermentation may be referred to as "biological degerming."

In the biological degerming processes of the present invention, the corn steeping and germ separation happen simultaneously with the yeast fermentation. The digestion of starch by added enzymes and yeasts during fermentation facilitate the release of the germ and pericarp. The germ and pericarp are removed during fermentation. In the biological degerming processes of the present invention, the germ is recovered during fermentation, after inoculation with yeast but prior to distillation.

Compared to conventional ethanol degerming processes, the biological degerming processes of the present invention have fractionation of the germ and pericarp during the fermentation process step. The biological degerming processes of the present invention produces co-products with better qualities over those produced in conventional ethanol processes. The co-products have enriched protein and reduced oil contents that can be easily tailored to produce feedstuffs with higher feed efficiency for different livestock needs. The biological degerming processes of the present invention also produce clean germ compared to conventional degerming processes, produce a high yield of oil from germ fractions, and have a similar ethanol yield and fermentation time as conventional dry-grind process.

The biological degerming processes of the present invention decrease throughput during distillation and decanting compared to conventional ethanol processes and have much lower energy usage compared to conventional dry-grind processes, lower water usage compared to conventional wet-milling processes, and have better separation of germs compared to other conventional techniques. The biological degerming processes of the present invention also utilize the conventional dry-grind plant infrastructure, which make it easier for industry to adapt. There is also a dramatic reduction of energy use and processing time by utilizing the biological degerming processes of the present invention.

Figure 5:
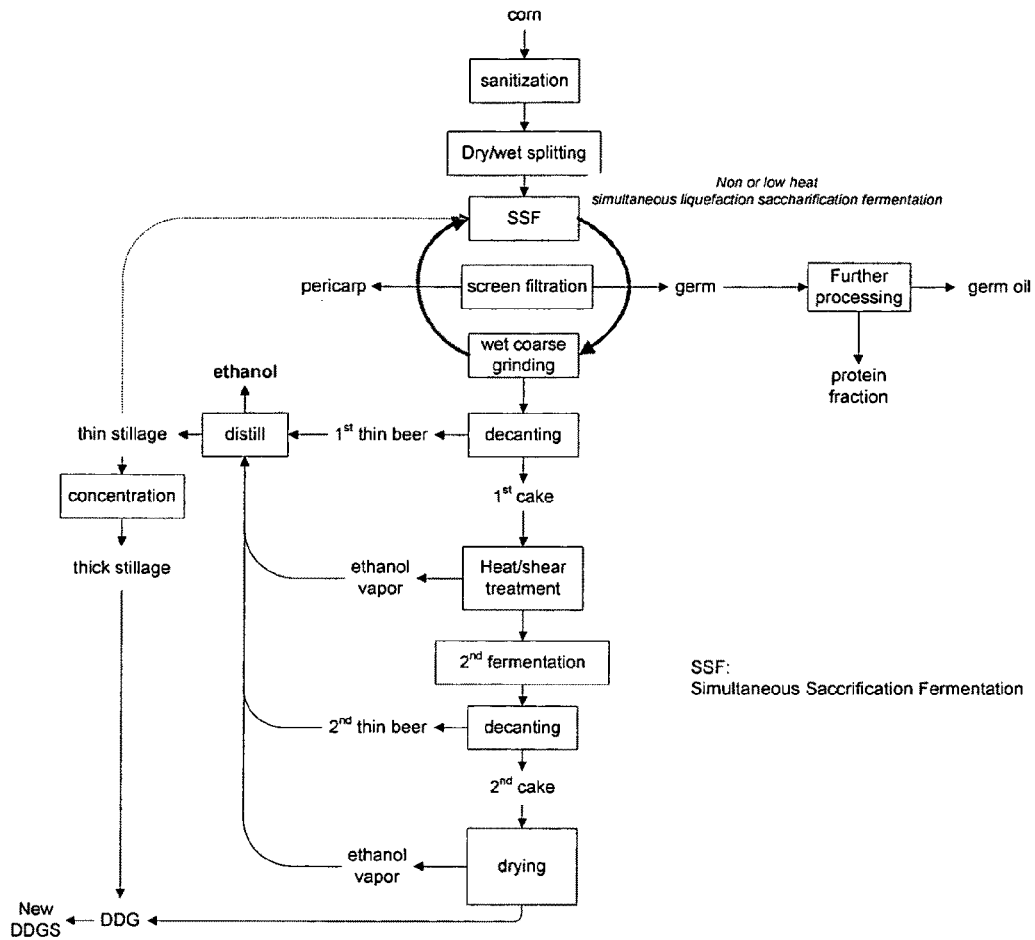
FIG. 5 shows an embodiment of the fermentation/biological degerming dry-grind corn ethanol process.
Figure 9:
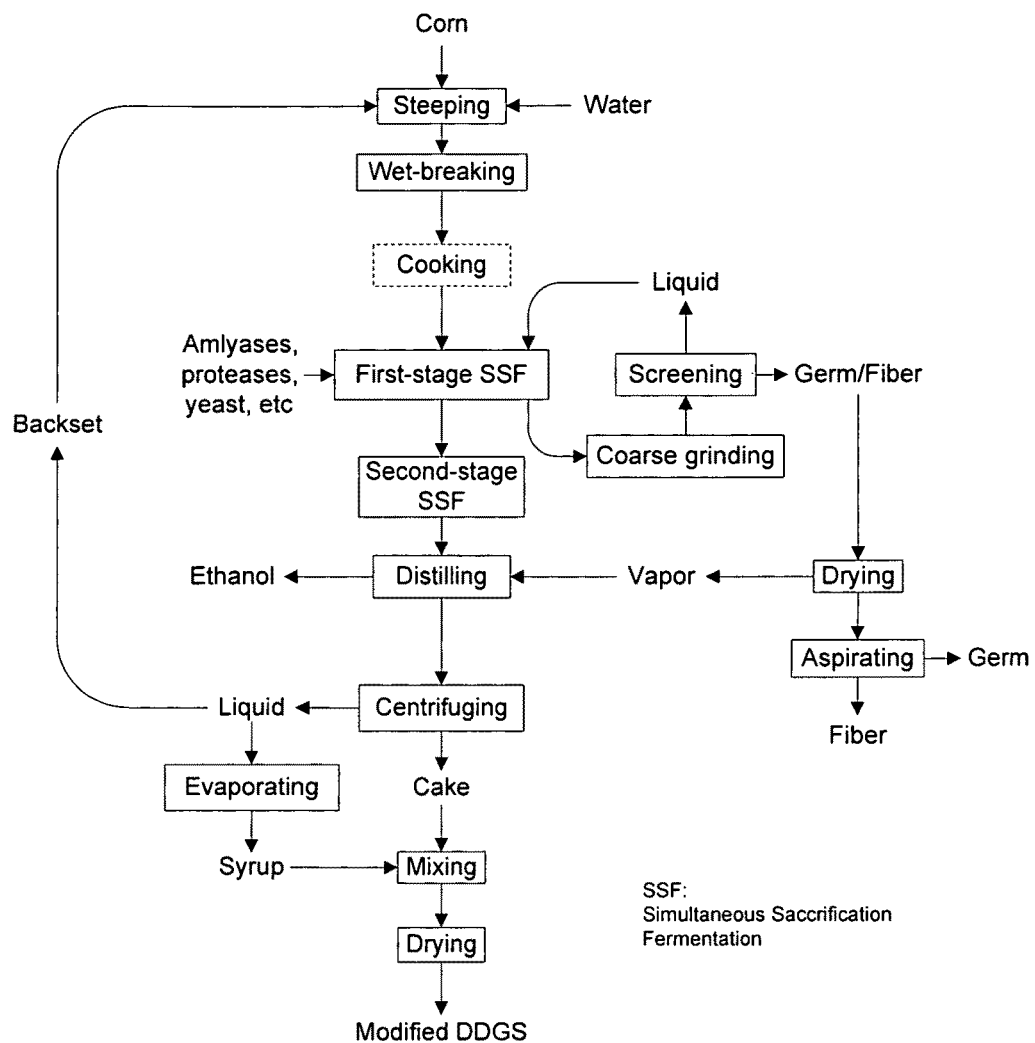
FIG. 9 shows an embodiment of the biological degerming ethanol process with pre-steeping dynamic simultaneous saccharification and fermentation without germ washing.
Figure 10:
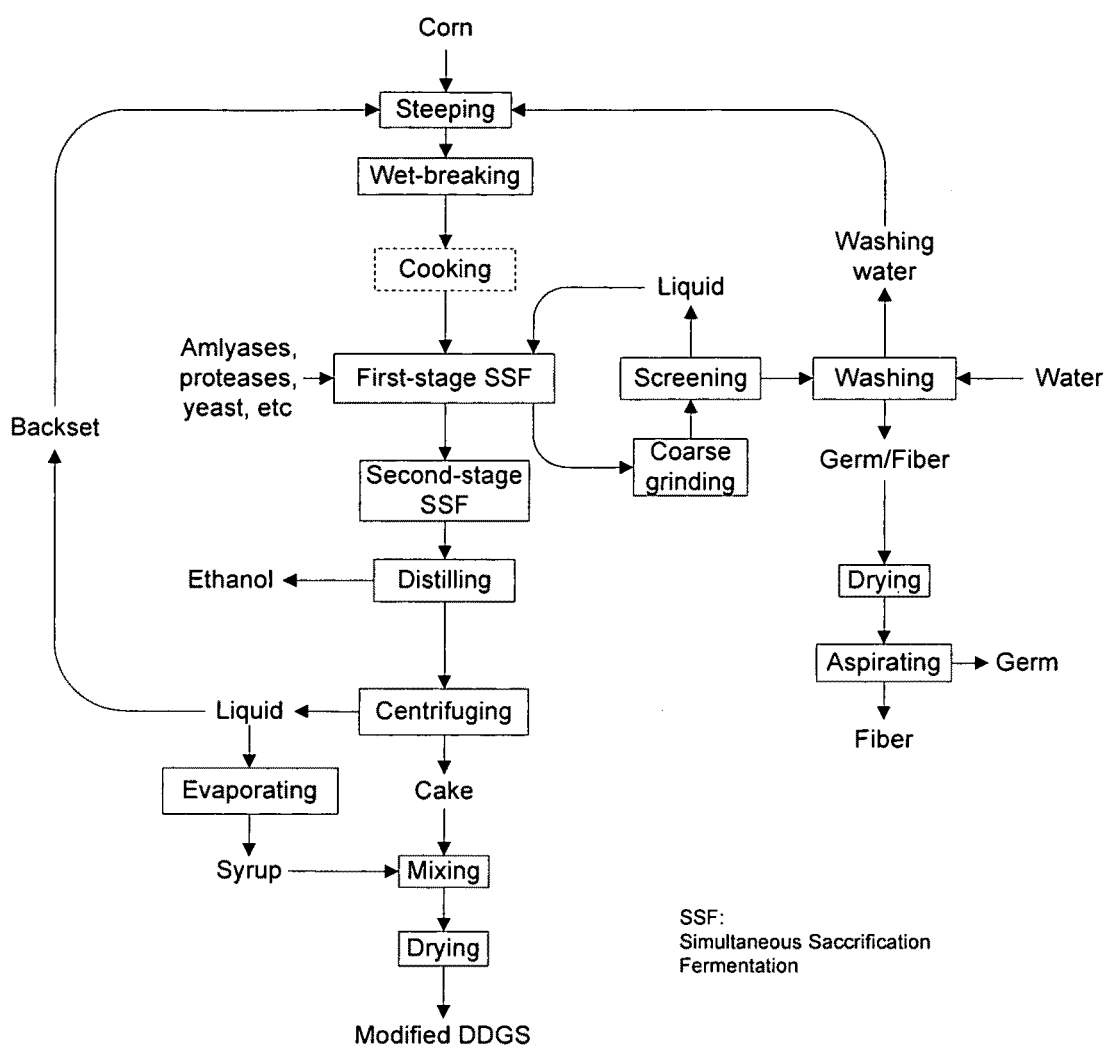
FIG. 10 shows an embodiment of the biological degerming ethanol process with pre-steeping dynamic simultaneous saccharification and fermentation with germ washing.
Figure 11:
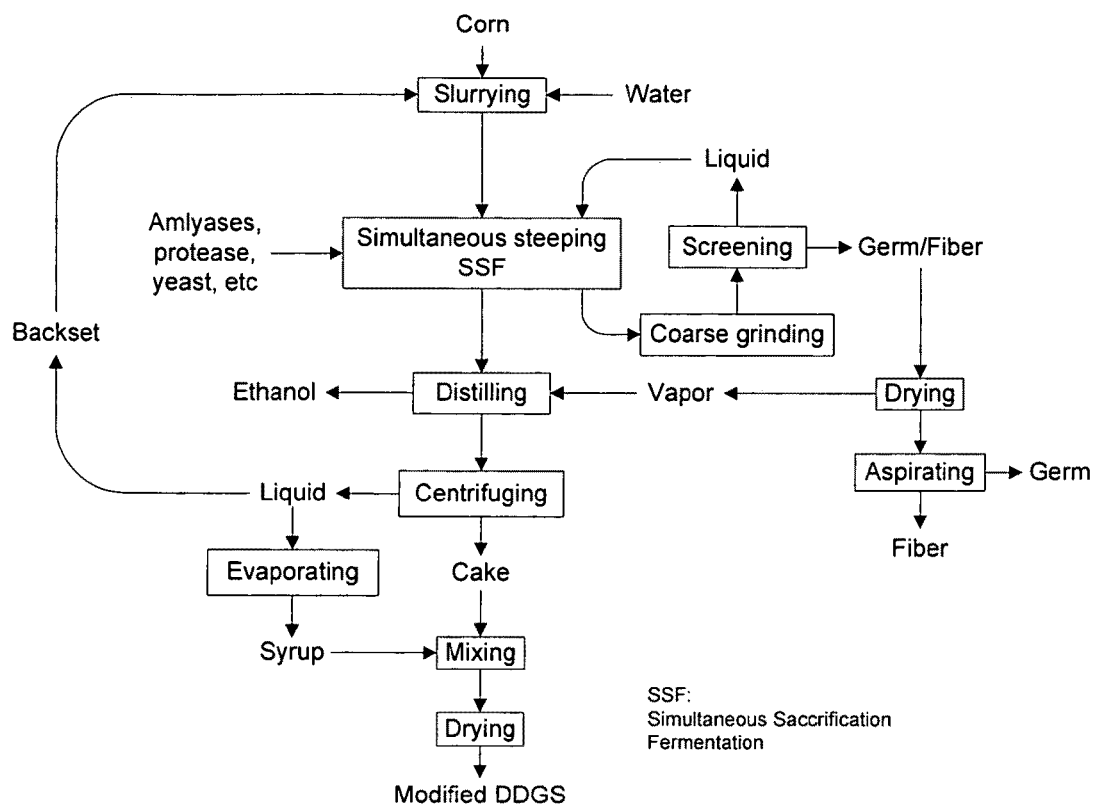
FIG. 11 shows an embodiment of the biological degerming ethanol process with simultaneous steeping and dynamic non-gelatinizing simultaneous saccharification and fermentation without germ washing.
Figure 12:
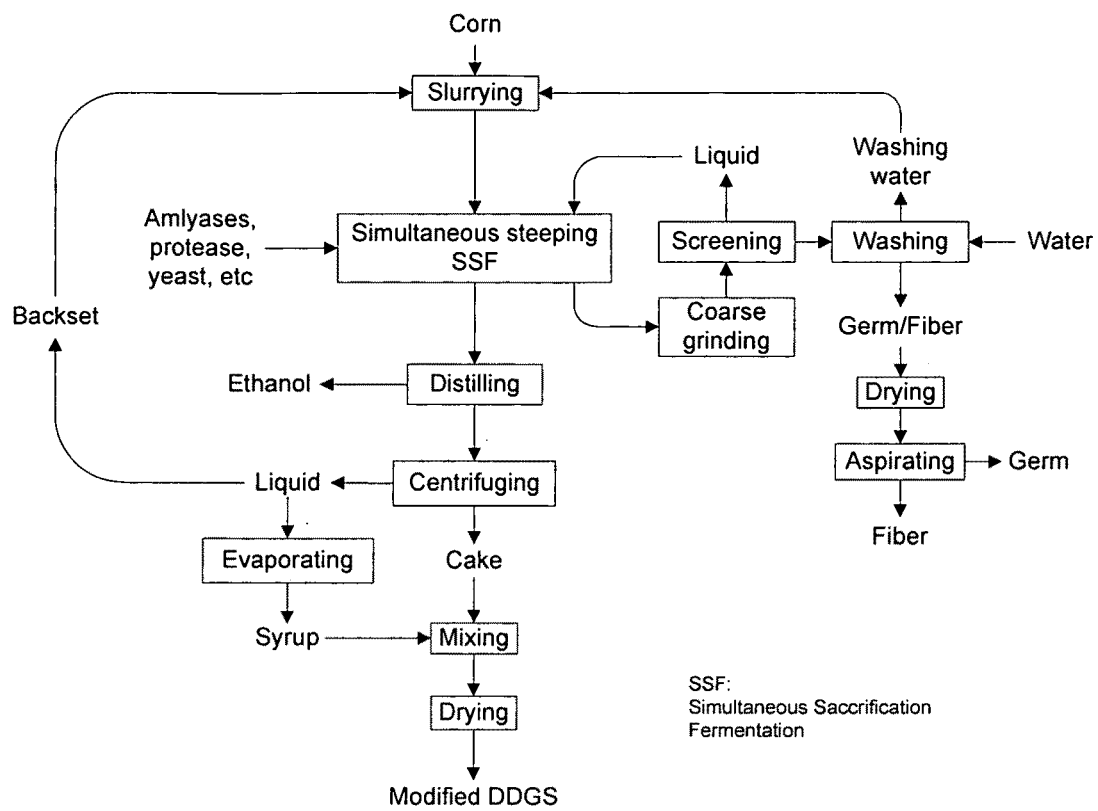
FIG. 12 shows an embodiment of the biological degerming ethanol process with simultaneous steeping and dynamic non-gelatinizing simultaneous saccharification and fermentation with germ washing.
Figure 13:
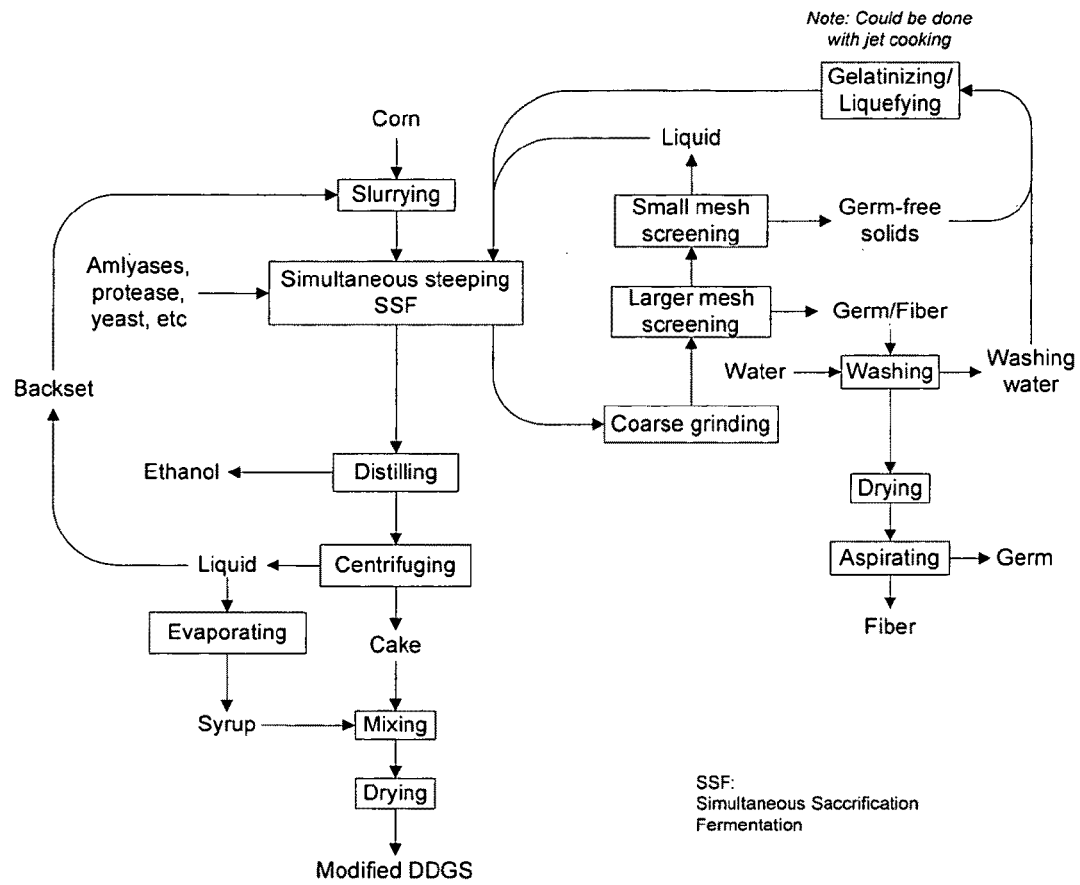
FIG. 13 shows an embodiment of the biological degerming ethanol process with simultaneous steeping and dynamic partial-gelatinizing simultaneous saccharification.

Referring now to FIGS. 5 and 9-13, multiple embodiments of the biological degerming ethanol process of the present invention are shown. FIG. 5 shows one aspect of the invention, referred to as the fermentation/biological degerming dry-grind corn ethanol process. FIG. 9 shows one aspect of the invention, referred to as the biological degerming design: pre-steeping dynamic SSF without germ washing. FIG. 10 shows one aspect of the invention, referred to as the biological degerming design: pre-steeping dynamic SSF with germ washing. FIG. 11 shows one aspect of the invention, referred to as the biological degerming design: simultaneous steeping and dynamic non-gelatinizing SSF without germ washing. FIG. 12 shows one aspect of the invention, referred to as the biological degerming design: simultaneous steeping and dynamic non-gelatinizing SSF with germ washing. FIG. 13 shows one aspect of the invention, referred to as the biological degerming design: simultaneous steeping and dynamic partial gelatinizing SSF. Referring now to FIGS. 5 and 9-13, multiple embodiments and aspects of the biological degerming process of the present invention are shown and described.

Referring now to FIG. 5, in one aspect of the present invention, the corn kernels are initially put through a steeping process. After the steeping period, the corn kernels may be opened in a dry/wet splitting process.

Referring now to FIGS. 9-10, in other aspects of the present invention, the corn kernels are initially put through a steeping process. Water is added for this process. In one aspect of the invention, referring now to FIG. 10, water may be recycled from a downstream washing step and adding to the steeping stage. After steeping, the corn kernels may be opened in a wet-breaking process.

Referring now to FIGS. 11-13, in other aspect of the present invention, the corn kernels are initially put through a slurrying process. Water is added to the corn kernels for the slurrying process. Referring now to FIG. 12, water may be added to the slurrying process step from a down-stream washing step. This water stream may be referred to as washing water. Referring now to FIGS. 11-13, water, referred to as backset, may be added to the slurrying process step. The backset may be produced at the downstream step of evaporating the liquid stream from the centrifuging process into syrup. The added backset may be in addition to or be the primary source of water for the slurrying step.

Referring now to FIG. 5, in one aspect of the invention, the opened corn stream may be sent to a simultaneous liquefaction saccharification fermentation process step. Enzymes, such as amylases and proteases as well as yeast, may be added to the slurry during this step. Concurrently with the SSF process step, the corn slurry is put through a wet coarse grinding step and also concurrently goes through a screen filtration step, separating the germ from the pericarp. In aspects of the invention, the corn steeping and germ separation happen simultaneously with the yeast fermentation. The digestion of starch by enzymes and yeasts facilitates the release of the germ and pericarp. Germ and pericarp are removed during fermentation.

Referring now to FIGS. 9-10, in other aspects of the invention, the opened corn may go through a cooking process step. The cooked, opened corn may then go through a first-stage pre-steeping dynamic SSF step. Enzymes, such as amylases and proteases as well as yeast, may be added to the slurry during this step. The corn slurry is put through a coarse grinding step and also goes through a screen filtration step, separating the germ/fiber fraction from the liquid fraction. The liquid may be recycled back to the first-stage pre-steeping dynamic SSF process.

Referring now to FIGS. 11-12, in other aspects of the invention, the slurried corn kernels may go through a simultaneous steeping and non-dynamic SSF process step. Enzymes, such as amylases and proteases as well as yeast may be added to the slurry during this step. The slurry is put through a coarse grinding step and also goes through a screen filtration step, separating the germ/fiber fraction from the liquid fraction. The liquid may be recycled back to the simultaneous steeping and non-dynamic SSF process step.

Referring now to FIG. 13, in other aspects of the invention, the slurried corn kernels may go through a simultaneous steeping and dynamic partial-gelatinizing SSF process step. Enzymes, such as amylases and proteases as well as yeast, may be added to the slurry during this step. The slurry is put through a coarse grinding step and also goes through a large-mesh screening step, separating the germ/fiber fraction from the slurry. The slurry then may be put through a small-mesh screening step, separating the liquid from the germ-free solids fraction. The liquid may be recycled for use back to the simultaneous steeping and dynamic partial-gelatinizing SSF process step. In one aspect of this invention, the germ-free solids fraction may be put through a gelatinizing/liquefying process step. In one aspect of this invention, this step alternatively could be done with jet cooking. Washing water may be added to the germ-free solids for the gelatinizing/liquefying process step from the downstream washing step. Liquid from the gelatinizing/liquefying step may be recycled for use back to the simultaneous steeping and dynamic partial-gelatinizing SSF process step.

Referring now to FIG. 5, in one aspect of this invention the separated germ fraction may go through further processing steps to separate the germ into germ oil and protein fraction. Referring now to FIGS. 9 and 11, in other aspects of this invention the separated germ/fiber fraction may go through a drying process step. The vapor produced in this drying process step may be recycled for used in the distilling step in the main process stream. After drying, the germ/fiber fraction may go through an aspirating process step to separate the germ/fiber fraction into a germ fraction and a fiber fraction. Referring now to FIGS. 10, 12 and 13, in other aspects of this invention the separated germ/fiber fraction may go through a washing process step. Water may be added to the germ/fiber fraction for the washing step. The germ/fiber fraction then may go through a drying step. After drying, the germ/fiber fraction may go through an aspirating process step to separate the germ/fiber fraction into a germ fraction and a fiber fraction. Referring now to FIGS. 10 and 12, the washing water from the washing step may be recycled for use in the earlier steeping process step in the main process stream. Referring now to FIG. 13, the washing water from the washing step may be recycled for use in the gelatinizing/liquefying of the germ-free solids fraction process step.

Referring now to FIG. 5, in one aspect of the invention, the slurry which has gone through the simultaneous liquefaction saccharification fermentation process step and concurrent wet coarse grinding and screen filtration may go through a decanting process step. The decanting step produces a first cake and a first thin beer. The first cake may then go through a heat/shear treatment step. The heat/shear treatment step produces ethanol vapor. The first cake is then put through a second fermentation step, and then another decanting step to produce a second cake and a second thin beer. The second cake is put through a drying process step to produce ethanol vapor and dried distillers grains (DDG). The first thin beer, the second thin beer, and the ethanol vapor produced in the heat/shear treatment of the first cake and the drying process step of the second cake may then distilled to produce ethanol and a thin stillage fraction. The thin stillage fraction may then be concentrated to produce thick stillage. The thick stillage may then be added to the DDG to produce new dried distillers grains with solubles (DDGS).

Referring now to FIGS. 9 and 10, the corn slurry which has gone through the first-stage simultaneous liquefaction saccharification fermentation process step and coarse grinding and screening steps may go through a second-stage simultaneous liquefaction saccharification fermentation process step. The slurry may then go through a distilling step to produce ethanol. Vapor from the drying of the germ/fiber fraction step may be added to the slurry for the distilling process step. The remaining slurry may then go through a centrifuging step to produce a liquid fraction and a cake fraction. The liquid fraction may go through an evaporation step to produce syrup. The leftover liquid, which may be referred to as backset, may be recycled and used in the upstream steeping step. The syrup may be mixed with the cake. The mixed syrup and cake may then go through a drying step to produce modified DDGS.

Referring now to FIGS. 11-13, the corn slurry which has gone through the simultaneous steeping and SSF may go through a distilling phase to produce ethanol. The remaining slurry may then go through a centrifuging step to produce a liquid fraction and a cake fraction. The liquid fraction may go through an evaporation step to produce syrup. The leftover liquid, which may be referred to as backset, may be recycled and used in the upstream slurrying step of the main process stream. The syrup may be mixed with the cake. The mixed syrup and cake may then go through a drying step to produce modified (DDGS).

In one aspect of the invention, the corn kernels may go through steeping and breaking process steps. The opened kernels may then go through a gelatinizing and liquefying step. Enzymes, such as α-amylase, may be added during this step. The slurry may then go through a germ/fiber screening step. The germ/fiber fraction may then be washed and then dried. The germ/fiber fraction may be aspirated to separate the germ from the fiber. The washing water from the washing step may be recycled for use in the steeping step. The germ/fiber free slurry produced from the screening step may then go through an SSF process step. Enzymes, such as amylases and proteases, as well as yeast may be added during this step. The slurry may then go through a distilling step to produce ethanol. The remaining slurry may go through a centrifuging step to produce a liquid fraction and a cake fraction. The liquid may go through an evaporating process step to produce syrup. The remaining liquid, which may be referred to as backset, may be recycled for use in the prior steeping step. The syrup may be mixed with the cake and then dried to produce modified DDGS.

All publications, patents and patent applications mentioned in the specification are indicative of the level of those skilled in the art to which this invention pertains. All such publications, patents and patent applications are incorporated by reference herein for the purpose cited to the same extent as if each was specifically and individually indicated to be incorporated by reference herein.

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications and alterations may be applied to the compositions and/or methods described herein without departing from the true spirit, concept and scope of the invention.

EXAMPLES

Example 1

Tail-End Degerming Ethanol Production Process

Figure 3:
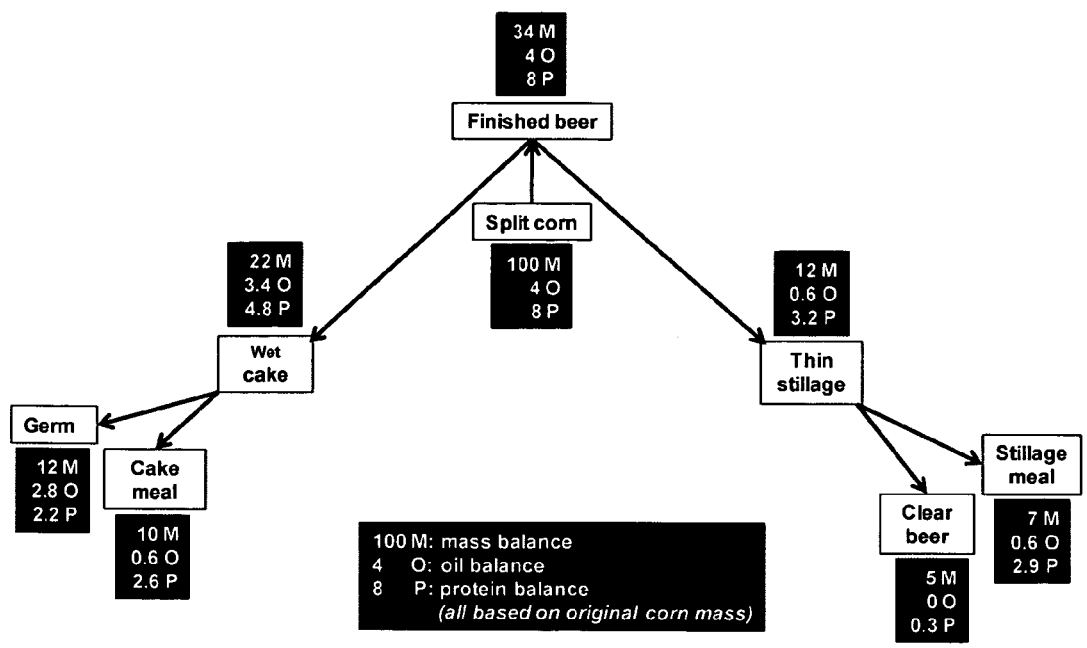
FIG. 3 is a diagram of different fraction distributions during the lab prototype process shown in FIG. 4.
Figure 4:
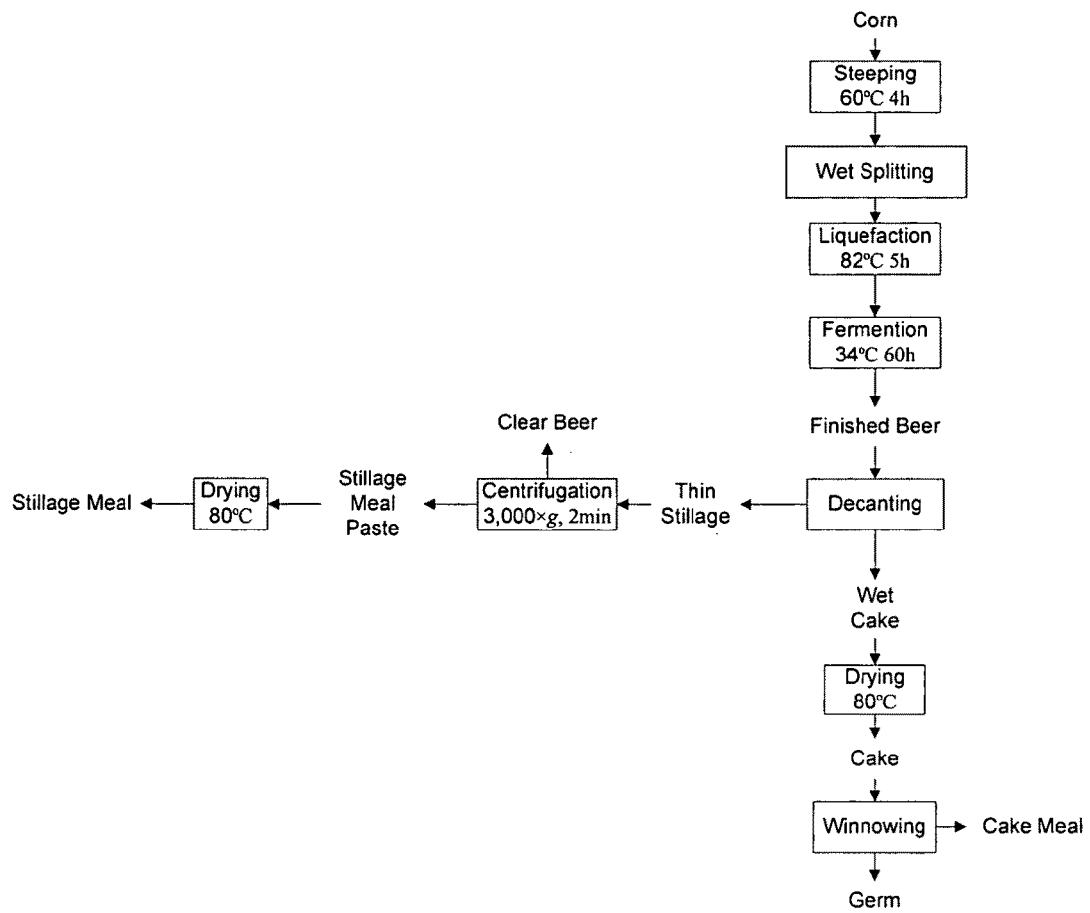
FIG. 4 shows a prototype of the tail-end degerming process used to produce the results shown in FIG. 3.

A lab prototype of one of the designs of the tail-end degerming ethanol process of the present invention was run and used to make the samples of FIG. 3. The lab prototype is shown in FIG. 4.

Corn samples were steeped in water at 60° C. for four hours. The steeped corn kernels were then opened by going through a wet-splitting process. The opened kernels were then liquefied by going through a liquefaction process. The slurry was held at 85° C. for five hours.

For fermentation, the corn slurry was cooled to 34° C. and held for 60 hours. After 60 hours of fermentation, the finished beer went through a decanting process (manual multiple wash-centrifuge filtration (MWCF) process step with two washes using a customer-designed device). The multiple wash-centrifuge filtration separated the finished beer into thin stillage and Wet cake fractions.

The thin stillage was put through a centrifugation process at 3000×g for two minutes. The centrifugation process separated the thin stillage into clear beer and stillage meal paste. The stillage meal paste was dried at 80° C. to produce stillage meal.

The wet cake was dried at 80° C. The cake was put through a winnowing step to produce cake meal and germ.

The Goldfish hexane extraction and the acid hydrolysis method were used to extract oil from the germ, cake meal and stillage meal. The following table shows the oil percentages recovered by these extraction methods used on the samples represented in FIG. 3.

TABLE 1

Oil and protein contents in the samples from tail-end-degerming process (on dry basis).

| Fraction | Oil content (%), by Goldfish hexane extraction | Oil content (%), by acid hydrolysis method | Protein content (%) |
|---|---|---|---|
| Germ | 29 | 31 | 22 |
| Cake meal | 6 | 8 | 28 |
| Stillage meal | 9 | 11 | 46 |

Experiment 2

Corn Treatment Experiments

Corn Samples and Fermentation Materials

No. 2 yellow dent corn from the 2007 crop year was acquired from the Heart of Iowa Cooperative (Nevada, Iowa). The corn was cleaned using a KICE laboratory aspirator (Model 6DT4, KICE Metal Products Co. Inc., Wichita, Kans.). Liquid α-amylase SPEZYME Xtra (13,642 α-amylase units/g, optimal pH of 5.0-6.7) and a saccharifying enzyme G-ZYME 480 Ethanol (401 glucoamylase units/g, optimal pH of 4.0-4.5), both from Genencor Inc. (Cedar Rapids, Iowa), were used to liquefy and saccharify the corn slurry, respectively. Lactrol (462 g of virginiamycin bioactivity/lb), an antibiotic extract, was from PhibroChem (Ridgefield Park, N.J.). Dry yeast (*S. cerevisiae*) Ethanol Red was acquired from Fermentis, a division of Lesaffre Yeast Corp. (Headland, Ala.). Urea was supplied by Keytrade USA Inc. (Kordova, Tenn.). All these fermentation materials were of industrial grade.

Corn Treatment

Five degerming treatments were studied. The treatments are summarized in Table 2.

the steeped corn was "split" by using a Roskamp smooth-surfaced roller mill (Model K, Roskamp Manufacturing, Inc., Waterloo, Iowa) with the roller gap fully open (the gap between the rollers was 3.45 mm or 0.136 inch). This gap setting was chosen to slightly break or crack the corn kernel

TABLE 2

Summary of different corn degerming and fermentation treatments

→ Treatment component (in time sequence) →

| No. | Treatment | Steeping | Kernel breaking | Degerming before fermentation | Fermentation | Degerming after fermentation |
|---|---|---|---|---|---|---|
| 1 | Front-end hand-dissect degerm fermentation* | ✓ | (hand dissecting + wet grinding) | (✓) | ✓ | x |
| 2 | Front-end wet-grind degerm fermentation | ✓ | Wet grinding | ✓ | ✓ | x |
| 3 | Tail-end wet-grind degerm fermentation | ✓ | Wet grinding | x | ✓ | ✓ |
| 4 | Tail-end wet-split degerm fermentation | ✓ | Wet splitting | x | ✓ | ✓ |
| 5 | No degerm fermentation (dry-grind) | x | Dry grinding | x | ✓ | x |

*For treatment 1, the kernel was first broken by hand-dissection, and then the germ-free fraction was wet-ground as in treatments 2 and 4.

In treatments 1 (front-end hand-dissect degerm fermentation) and 2 (front-end wet-grind degerm fermentation) the germ was recovered before fermentation, while in treatments 3 (tail-end wet-split degerm fermentation) and 4 (tail-end wet-grind degerm fermentation), the germ was recovered after fermentation. Treatment 5 was the typical dry-grind ethanol fermentation without degerming since the whole kernel including the germ was ground into meal, making the germ particles too fine to be practically recoverable. For better understanding, the treatment details were described in the sequence of processing across different treatments as follows.

Corn Steeping

For all treatments, 500 g of corn (dry basis) was used. In treatments 1-4, the corn was steeped in deionized water at 52° C. for 36 h with corn:water ratio of 2:3 (w/w). After steeping, the steeping liquid was drained, leaving the corn kernels with moisture content about 33 percent (determined by drying at 130° C. for 3 h). The resulting steeping liquor was included in the fermentation. No steeping was conducted in treatment 5.

Kernel Breaking and Size Reduction

In treatment 1, 750 g of steeped corn (about 500 g dry basis) was hand-dissected to remove the germ. The germ-free fraction was mixed with 750 g of water and steeping liquor and ground in 6 equal batches by using a Waring Commercial Blendor (Model 51BL31, Waring Products, Inc., Torrington, Conn.) equipped with a customer-made blunt blade inside a glass cup with capacity of 1,183 mL (40 oz). The blender was operated on the low setting through a Staco variable autotransformer (Type 3PN2210, Staco Energy Products, Co., Dayton, Ohio) set at 35 percent of the 120 voltage for 5 min. The same grinding step was applied to treatments 2 and 3 (750 g of steeped corn with 750 g of water/steeping liquor and ground in 6 batches). This method was a modification of Eckhoff et al., which simulates the coarse grinding in the wet-milling process. For treatment 4, so that the kernel remained as one piece without major damage to the germ. In treatment 5, the dry corn was ground by using a Fitz Mill (Model DAS 06, Fitzpatrick Co., Elmhurst, Ill.) at 5,000 rpm with a 3-mm round-hole screen. The resulting corn meal had a similar particle size distribution profile as the meal used in commercial dry-grind ethanol plant (data not shown).

Degerming

In treatments 1 and 2, the germ was recovered before fermentation (front-end). In treatment 1, the kernel was hand dissected to expose the germ and the germ was removed by using pointed tweezers. Care was taken to ensure the integrity and clean separation of germ from endosperm and pericarp. In treatment 2, the germ fraction was recovered by using a scoop made of copper mesh with 7-mesh openings while stirring the ground slurry to float the germ pieces. The non-floating large germ pieces were hand-picked from the residual solids after the slurry was filtered through a 7-mesh sieve. The degermed solids (mainly consisting of large pericarp and endosperm pieces) and liquid (starchy slurry with solids fines) were then combined to form the degermed slurry for fermentation. In treatments 3 and 4, germ pieces were isolated after fermentation (tail-end). The germs were hand-picked from the solids after the beer was filtered through a 7-mesh sieve. The recovered germ included the intact germ and large broken pieces that were retained by 7-mesh sieve. A few intact germs with similar size and shape from each treatment were sampled and stored at 5° C. in a sealed plastic bag for physical strength analysis. The germ fraction from each treatment was dried at 80° C. for 3 hours and sealed in a plastic bag for oil extraction and analysis. The drying conditions were chosen to minimize possible heating damage to the germ oil.

Ethanol Fermentation

A modified laboratory dry-grind corn ethanol fermentation procedure was used for all corn samples. No additional autoclaving or jet-cooking was used in this study. The cooking and liquefaction were carried out simultaneously at 82° C. for 4 hours with constant stirring using a setup consisted of a stirrer (Fisher Scientific, Dubuque, Iowa), a button-type glass shaft and a polytetrafluoroethylene (PTFE) blade. Two mL α-amylase was used. The fermentation was carried out in a LAB-LINE Incubator-Shaker (Model 3525, Lab-line Instruments Inc., Melrose Park, Ill.) at 34° C. with 100 rpm shaking for 60 hours. After fermentation, the finished beer was heated at 70° C. for 20 min to inactivate the yeast. An elastic film was used to seal the mouth of the flask to prevent ethanol loss during heating.

Ethanol Yield Quantification

The ethanol yield was calculated based mass loss during fermentation. The ethanol, lactic and acetic acid concentrations in the finished beer were measured by high pressure liquid chromatography (HPLC).

Germ Characterization

Germ Yield, Oil Content and Germ Breakage

The germ yield was calculated as the percentage of germ fraction based on original corn. Germ was pre-ground using a mortar and a pestle to about 20-mesh. Germ oil was extracted with hexane with germ:solvent ratio of 1:5 (w/v) and constant stirring for 30 min.

Four stages of extractions were carried out for one sample. Solids and liquid were separated by vacuum filtration with filter paper. Hexane was desolventized by a rotary evaporator (Rotavapor R-124, Buchi, Switzerland). In order to achieve maximum recovery of the free fatty acid, chloroform-methanol (2:1, v/v) was also tested with the same ratio and extraction times for comparison. Hexane recovered 94 percent of the total lipid and 90 percent of the free fatty acids based on extraction with chloroform-methanol. Because chloroform-methanol and germ mixture was difficult to filter and chloroform-methanol extracted significant amount of non-liquid components, which need multiple steps of purification, we chose hexane as the extraction solvent. Oil content in the germ is the percentage oil of dry germ. Germ breakage is derived from oil extraction data:

$$\text{Germ breakage}(\%) = \left(1 - \frac{\text{total oil in the recovered germ}}{\text{total theoritical germ oil}}\right) \times 100$$

Where the total oil in the hand dissected germ fraction was considered the "total theoretical germ oil" and the "recovered germ" was the germ fractions that were larger than the opening of 7-mesh sieve. This parameter was used to quantity the amount of germ broken into fine pieces that ended up in the degermed fractions. Since the calculation is based on germ oil partitioning, it does not measure the absolute number of small germ pieces. The method can also test if oil leaches out the germ without further apparent physical damage of the germ. The acid hydrolysis method was used to quantify oil content in the degermed DDGS after the degermed beer was evaporated at 80° C. It is used to verify the germ oil partition in the recovered germs and degermed DDGS.

Physical Strength of the Germ

The physical strength of the wet germ was analyzed using a texture analyzer (Model TA-XT2i, Texture Technologies Corp., Scarsdale, N.Y.) with a TA-10 probe and a TA-90A plate at ambient temperature. The press distance was set at 80 percent with probe moving speed of 0.20 mm/s. The physical strength of the germ was expressed as the resistance force profile during pressing in which the probe pressed to 80 percentage of the germ's original thickness at constant speed.

Germ Oil Quality Analyses

Free Fatty Acid Content

Free fatty acids were isolated and quantified by using thin layer chromatography (TLC) plates Silica Gel G 500 (Analtech Inc., Newark, Del.) with hexane/ethyl ether/acetic acid (80/20/1, v/v/v) as the mobile phase. The free fatty acid band was detected after spraying with 2',7'-dichlorofluorescein and viewing under UV light and the band was scraped off the plate. Free fatty acids were converted to methyl esters with 3 percentage sulfuric acid in methanol (v/v) at 65° C. for 3 hours. The composition of free fatty acids was obtained using a Hewlett Packard gas chromatograph (Model 589 Series II, Hewlett-Packard Co., Avondale, Pa.) with a fused-silica capillary column (Model SP-2423 Supelco, Inc., Bellefontaine, Pa.), which had a dimension of 30 m×0.25 mm i.d. and a film thickness of 0.2 μm. Helium was used as the carrier gas at 1.9 mL/min flow rate. The temperature profile of the oven was programmed to heat from 150 to 180° C. over 6 min and then hold at 180° C. for 20 min. Methyl heptadecanoate was used as an internal standard for FAME quantification.

Peroxide Value

The peroxide value of the germ oil was measured according to a standard AOCS redox titration.

Experimental Design and Statistical Analysis

All the treatments were randomized with two replicates for each treatment. Statistical analysis was performed using General Linear Model procedures of SAS 9.1.

Results and Discussion

Treatment 1 represents ideal degerming and the best oil quality since the germ was isolated by hand dissection before cooking and fermentation, while treatment 5 represents the least degerming and the worst oil quality since the germ was broken up into fine pieces and went through the entire fermentation process. Treatments 2 and 3 were used to compare the effect of yeast fermentation on germ and oil quality since the corn was wet-ground in the same way but the germ was recovered at different locations in the process (before and after fermentation, or front- and tail-end, respectively). Treatment 4 was designed to not only test the effect of fermentation on germ and germ oil quality but also to test the effect of low shear kernel breaking method (wet-split), which was expected to have much less damage to the germ compared to grinding in the wet-degerming process.

Fermentation Performance

The low lactic and acetic levels indicate that microbial contamination during fermentation was under control. The ethanol yields for most of the treatments were ~35 percent, similar to commercial dry-grind ethanol yield (communications with industry personnel) except for treatment 4 (tail-end wet-split degerm fermentation), which was ~10 percent lower than the rest (see Table 4). The low ethanol yield was attributed to incomplete hydrolysis of starch upon visual examination. The finished beer from treatment 4 contained large pericarp and endosperm pieces and a few whole kernels. Starch granules in the middle of the large endosperm pieces eluded hydrolysis by amylases and eventual conversion by the yeast. It should be noted that a conservative wet-split condition was chosen to avoid major damage to the germ since the objective of this study was to investigate the fate of germ during fermentation, not yet to optimize the ethanol yield. It was believed that improved splitting/cooking/blending could reduce the amount of undigested starch while maintaining germ integrity.

After fermentation of treatment 4 (tail-end wet-split degerm fermentation), a few intact germs were visible as white pieces in the yellow background, which was the color of large pericarp pieces and endosperm proteins. Some germ pieces were loosely attached to the pericarp at the tip cap section. The pale color of the germ was probably because of the much lower carotenoid level in the germ compared to the endosperm. When the white starch granules disappeared during ethanol fermentation, the carotenoid pigments were concentrated and became more pronounced in the residual, which act as a yellow background for the pale germs.

TABLE 3

Fermentation results of different corn degerming and fermentation treatment

| No. | Treatment | Ethanol conc. in beer by HPLC (%, w/v) | Ethanol yield, based on mass loss (%) | Lactic acid conc. in beer by HPLC (%, w/v) | Acetic acid conc. in beer by HPLC (%, w/v) |
|---|---|---|---|---|---|
| 1 | Front-end hand-dissect degerm | $16.57^{ab}$ | $34.76^a$ | $0.16^a$ | $0.08^c$ |
| 2 | Front-end wet-grind degerm | $16.99^a$ | $34.78^a$ | $0.16^a$ | $0.10^b$ |
| 3 | Tail-end wet-grind degerm | $16.31^{ab}$ | $35.33^a$ | $0.18^a$ | $0.08^c$ |
| 4 | Tail-end wet-split degerm | $14.82^c$ | $31.36^b$ | $0.12^{ab}$ | $0.08^c$ |
| 5 | No degerm (dry-grind) | $16.10^b$ | $34.67^a$ | $0.04^b$ | $0.14^a$ |

Note:
Means within a column followed by different superscripts are significantly different at P Degerm Results and Germ Characterization.
Germ Yield, Oil Content and Germ Breakage:

Since front-end had-dissection theoretically removed all the germs, treatment 1 had the highest germ yield and germ oil yield. Treatment 4 (tail-end wet-split) achieved the same germ oil yield, indicating that all germ was recovered. The germ yield was slightly lower but the germ oil content was slightly higher (although not significant) than those of treatment 1, probably because more non-lipid components were leached out during the long fermentation process, similar to that in the steeping step of conventional wet-milling (see Table 4). These results confirmed that the germ remained as a whole piece during fermentation.

Germ yield and germ oil yield for treatment 2 (front-end wet-grind degerm) were significantly lower than for treatments 1 and 4, showing that wet-grinding significantly damaged the germ. When the corn was wet-ground in the same way but was degermed at the tail-end (treatment 3), the germ yield and germ oil yield were further significantly decreased.

TABLE 4

Germ yields and oil contents for different corn degerming and fermentation treatments

| No. | Treatment name | Germ yield (%) | Germ oil yield (%, on original corn) | Oil content in germ (%) |
|---|---|---|---|---|
| 1 | Front-end hand-dissect degerm | $7.91^a$ | $2.64^a$ | $33.50^b$ |
| 2 | Front-end wet-grind degerm | $6.16^c$ | $2.06^b$ | $34.09^b$ |
| 3 | Tail-end wet-grind degerm | $4.04^d$ | $1.58^c$ | $39.16^a$ |
| 4 | Tail-end wet-split degerm | $7.26^b$ | $2.64^a$ | $36.40^{ab}$ |
| 5 | No degerm (dry-grind) | $0.00^e$ | $0.00^d$ | $7.17^{c,\,*}$ |

* Oil in the whole dried DDGS since no degerming was performed. Means within a column followed by different superscripts are significantly different at P < 0.05.

Higher germ breakage indicates more damage to the germ. Hand-dissection (treatment 1) and dry-grinding (treatment 5) represent two extremes for germ breakage (0 percent vs. 100 percent breakage). The germ from tail-end wet-split fermentation (treatment 4) had near zero breakage, indicating that kernel breaking, cooking, hydrolysis and yeast fermentation did not significantly damage the germ. It also indicated that the germ matrix remained strong and intact without any leaching of oil. Wet-grinding produced 22 percentage germ breakage (treatment 2) before fermentation. The breakage was mainly due to the small fractured germ pieces were not recovered by a 7-mesh sieve. When degermed at the tail-end after fermentation (treatment 3), the germ breakage increased to about 40 percentage. The additional breakage may be from the small germ pieces that were previously attached to the large germ pieces in the corn slurry after wet-grinding but had broken loose during the blending and shaking in the fermentation process as the starch was digested. This increased breakage may also indicate that if the germ was damaged by rough grinding, it may be more easily degraded during fermentation than if the germ is more intact.

The germ oil yield has a strong negative linear relationship with residual oil content in the degermed DDGS. Treatments 1 and 4 (front-end hand-dissect and tail-end wet-split) had the same oil yields and similar residual oil contents in DDGS. More germ oil was lost in DDGS in treatment 2 (front-end wet-grind) and was lost even more in treatment 3 (tail-end wet-grind). This observation confirmed that the decreased germ oil yield was due to fine germ pieces lost in DDGS, not because of metabolic consumption by the yeast. In treatment 1 (front-end hand-dissect), all germ was removed but the germ-free DDGS still contained measurable oil by using the acid hydrolysis method. Oil exists in pericarp and endosperm in low concentration. Since the majority of the corn oil is present in the germ, the minor amount non-germ oil was not the focus of the present study.

Physical Strength of the Germ

The comparison between the physical strength of the germ before and after fermentation can offer a clue as to why the germ can (or cannot) survive fermentation. Germ is the embryo of corn and it does not have homogenous texture nor are its shape and structure identical from one kernel to another. This brings some challenges to the quantitative analysis of germ physical strength and considerable measurement variations were observed. No significant strength difference was found between the germ isolated before fermentation and after fermentation. One explanation may be the unique structure and composition of the germ. Germ does not contain significant amount of starch or water-soluble components that can cause the germ structure to collapse during cooking or hydrolysis. The germ internal cellular structure is after soaking and can resist low shear blending, and the rubbery texture did not change during fermentation.

Germ Oil Quality

Free Fatty Acid Content

The free fatty acid contents of the germ fractions from treatments 1-4 were all about 2 percentage. There was no significant difference between the oil extracted from the front-end and the tail-end germs. Intact or large germ pieces appear to have protected the oil from enzymatic hydrolysis. On the contrary, oil from dry-grind ethanol process was highly hydrolyzed, containing about 22 percent free fatty acids. It is suspected that the hydrolysis was caused by endogenous lipase released by dry-grinding or exogenous enzymes secreted by yeast, or both.

Peroxide Value

The peroxide value showed a similar result to that of free fatty acids. Germ oil from tail-end wet-split treatment, which endured 4 h of cooking and liquefying and 60 hours of fermentation, had the same peroxide value as that from front-end wet-grind and front-end hand-dissection. It can be explained by two reasons, one is that when germs maintain their original structure, the oil existed in oil bodies which are remarkably stable to oxidation and other physiochemical attacks to the oil; the second is that the ethanol fermentation creates an anaerobic environment (oxygen free in the mash). Germ oil from tail-end wet-grind treatment had significantly higher peroxide value than that from front-end, although the difference was relatively small (<1 meq/kg). The small increase in peroxide value most likely happened during the cooking/liquefying steps considering the germ was partially damaged by wet-grinding. On the other hand, oil from the dry-grind process had the highest peroxide value (9 meq/kg) compared to an average of 2 meq/kg for the other oils. We believe this was because the dry-grind broke germs into small pieces, exposing more oil to the oxygen before and after the fermentation.

This study has shown that germs can maintain their physical structures during starch cooking, hydrolysis and yeast fermentation steps of the ethanol fermentation process and the oil in the germ fraction remains in its native quality. This suggests that the germ recovered during or after fermentation process may be used to produce food-grade oil or a better oil feedstock for manufacturing biodiesel than oil recovered from traditional dry-grind ethanol production. Integrating this novel degerming concept into dry-grind ethanol production also produces value-enhanced DDGS products to meet the needs of swine and poultry feeding operations, which usually require different protein, oil and fiber contents than is produced in normal dry-grind ethanol plants without front-end degerming or tail-end oil recovery. These findings lay the foundation for developing a series of new degerming strategies for the dry-grind ethanol industry.

We claim:

1. A corn fermentation method comprising:
    a) providing whole corn kernel as corn material;
    b) simultaneously steeping, breaking, gelatinizing and liquefying said whole corn kernel in water with a roller mill with a gap of 3.45 mm and in the presence of enzymes, said gelatinizing and liquefying steps being performed at a temperature of 75° C. to 95° C., and said steeping step lasting for no more than 4 hours to produce a slurry whose germ retains its physical structure;
    c) fermenting the slurry whose germ retains the physical structure thereof;
    d) distilling a fermented slurry to produce ethanol, wherein germ in the fermented slurry retains the physical structure thereof;
    e) after the step of distilling, separating the fermented slurry into a wet cake fraction whose germ retains the physical structure thereof, and a stillage fraction;
    f) drying the wet cake fraction whose germ retains the physical structure thereof;
    g) separating a germ fraction of retaining the physical structure thereof and a cake meal fraction from a dried wet cake fraction;
    h) extracting oil from the germ fraction of retaining the physical structure thereof; and
    i) isolating a fiber rich fraction and a protein rich fraction from the cake meal fraction.

2. The corn fermentation method of claim 1 wherein the fermenting step is performed simultaneously with a process of saccharification.

3. The corn fermentation method of claim 1 further comprising a step of coarsely grinding the corn material concurrently with the simultaneously performed processes of steeping, breaking, gelatinizing and liquefying.

4. The corn fermentation method of claim 1 wherein the step g) further comprising winnowing or aspirating the dried wet cake fraction.

* * * * *